US008409132B2

(12) United States Patent
Ferren et al.

(10) Patent No.: US 8,409,132 B2
(45) Date of Patent: *Apr. 2, 2013

(54) TREATMENT INDICATIONS INFORMED BY A PRIORI IMPLANT INFORMATION

(75) Inventors: Bran Ferren, Beverly Hills, CA (US); Roderick A. Hyde, Redmond, WA (US); Muriel Y. Ishikawa, Livermore, CA (US); Eric C. Leuthardt, St. Louis, MO (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1171 days.

This patent is subject to a terminal disclaimer.

(21) Appl. No.: 12/005,122

(22) Filed: Dec. 20, 2007

(65) Prior Publication Data
US 2009/0157055 A1 Jun. 18, 2009

Related U.S. Application Data

(63) Continuation-in-part of application No. 12/004,107, filed on Dec. 18, 2007.

(51) Int. Cl.
*A61M 31/00* (2006.01)
(52) U.S. Cl. ...................................... 604/65; 604/891.1
(58) Field of Classification Search .................... 604/65, 604/66, 67, 266, 891.1
See application file for complete search history.

(56) References Cited

U.S. PATENT DOCUMENTS

| 3,409,008 A | 11/1968 | Mortensen et al. |
| 3,673,189 A | 6/1972 | Curran et al. |
| 4,039,665 A | 8/1977 | Foley |
| 4,138,156 A | 2/1979 | Bonner |
| 4,303,984 A | 12/1981 | Houvig |
| 4,312,358 A | 1/1982 | Barney |
| 4,321,929 A | 3/1982 | Lemelson et al. |
| 4,379,461 A | 4/1983 | Nilsson et al. |
| 4,536,274 A | 8/1985 | Papadakis et al. |
| 4,569,355 A | 2/1986 | Bitterly |
| 4,629,336 A | 12/1986 | Ishizaka |
| 4,649,933 A | 3/1987 | Jackson |
| 4,689,041 A | 8/1987 | Corday et al. |
| 4,756,310 A | 7/1988 | Bitterly |
| 4,804,054 A | 2/1989 | Howson et al. |

(Continued)

FOREIGN PATENT DOCUMENTS

| JP | 7059754 A | 3/1995 |
| WO | WO 94/14487 | 7/1994 |

(Continued)

OTHER PUBLICATIONS

Butty, V.D. et al.; "Residence Times and Basins of Attraction for a Realistic Right Internal Carotid Artery With Two Aneurysms"; Biorheology; 2002; pp. 387-393; vol. 39; IOS Press.

(Continued)

*Primary Examiner* — Bhisma Mehta

(57) ABSTRACT

Systems and methods are described for implementing or deploying therapeutic administration systems for obtaining a flow-change-indicative measurement and signaling a decision whether to administer one or more clot-reducing agents at least partly based on the flow-change-indicative measurement.

21 Claims, 13 Drawing Sheets

U.S. PATENT DOCUMENTS

| | | |
|---|---|---|
| 4,819,658 A | 4/1989 | Kolodner |
| 4,820,261 A | 4/1989 | Schmoll et al. |
| 4,860,751 A | 8/1989 | Callaghan |
| 4,981,596 A | 1/1991 | Shiino et al. |
| 5,012,411 A | 4/1991 | Policastro et al. |
| 5,036,462 A | 7/1991 | Kaufman et al. |
| 5,103,827 A | 4/1992 | Smith |
| 5,153,827 A | 10/1992 | Coutré et al. |
| 5,178,153 A | 1/1993 | Einzig |
| 5,188,106 A | 2/1993 | Nappholz et al. |
| 5,201,318 A | 4/1993 | Rava et al. |
| 5,242,382 A | 9/1993 | Gorsuch et al. |
| 5,243,998 A | 9/1993 | Silverman et al. |
| 5,256,538 A | 10/1993 | Aiken et al. |
| 5,262,669 A | 11/1993 | Wakatabe et al. |
| 5,282,467 A | 2/1994 | Piantadosi et al. |
| 5,305,745 A | 4/1994 | Zacouto |
| 5,335,313 A | 8/1994 | Douglas |
| 5,348,002 A | 9/1994 | Caro |
| 5,348,015 A | 9/1994 | Moehring et al. |
| 5,360,005 A | 11/1994 | Wilk |
| 5,429,137 A | 7/1995 | Phelps et al. |
| 5,438,983 A | 8/1995 | Falcone |
| 5,441,051 A | 8/1995 | Hileman et al. |
| 5,443,440 A | 8/1995 | Tumey et al. |
| 5,445,616 A | 8/1995 | Kratoska et al. |
| 5,474,574 A | 12/1995 | Payne et al. |
| 5,497,787 A | 3/1996 | Nemesdy et al. |
| 5,508,203 A | 4/1996 | Fuller et al. |
| 5,524,636 A | 6/1996 | Sarvazyan et al. |
| 5,546,955 A | 8/1996 | Wilk |
| 5,558,638 A | 9/1996 | Evers et al. |
| 5,576,952 A | 11/1996 | Stutman et al. |
| 5,593,431 A | 1/1997 | Sheldon |
| 5,601,811 A | 2/1997 | Gallagher et al. |
| 5,620,475 A | 4/1997 | Magnusson |
| 5,628,322 A | 5/1997 | Mine |
| 5,662,109 A | 9/1997 | Hutson |
| 5,671,750 A | 9/1997 | Shinoda |
| 5,684,460 A | 11/1997 | Scanlon |
| 5,699,934 A | 12/1997 | Kolcun et al. |
| 5,713,858 A | 2/1998 | Heruth et al. |
| 5,718,247 A | 2/1998 | Frankel |
| 5,722,972 A | 3/1998 | Power et al. |
| 5,724,983 A | 3/1998 | Selker et al. |
| 5,725,492 A | 3/1998 | Igo et al. |
| 5,740,540 A | 4/1998 | Emmermann |
| 5,755,571 A | 5/1998 | Companion |
| 5,755,741 A | 5/1998 | Vogel |
| 5,769,801 A | 6/1998 | Tumey et al. |
| 5,793,969 A | 8/1998 | Kamentsky et al. |
| 5,795,327 A | 8/1998 | Wilson et al. |
| 5,807,261 A | 9/1998 | Benaron et al. |
| 5,832,182 A | 11/1998 | Zhang et al. |
| 5,833,603 A | 11/1998 | Kovacs et al. |
| 5,840,049 A | 11/1998 | Tumey et al. |
| 5,857,998 A | 1/1999 | Barry |
| 5,879,292 A | 3/1999 | Sternberg et al. |
| 5,886,142 A | 3/1999 | Thakur et al. |
| 5,892,570 A | 4/1999 | Stevens |
| 5,911,689 A | 6/1999 | Smith et al. |
| 5,925,016 A | 7/1999 | Chornenky et al. |
| 5,931,797 A | 8/1999 | Tumey et al. |
| 5,935,075 A | 8/1999 | Casscells et al. |
| 5,935,099 A | 8/1999 | Peterson et al. |
| 5,941,829 A | 8/1999 | Salzstein et al. |
| 5,942,986 A | 8/1999 | Shabot et al. |
| 5,960,797 A | 10/1999 | Kramer et al. |
| 5,963,997 A | 10/1999 | Hagopian |
| 5,967,986 A | 10/1999 | Cimochowski et al. |
| 5,978,693 A | 11/1999 | Hamilton et al. |
| 5,983,429 A | 11/1999 | Stacy et al. |
| 5,987,345 A | 11/1999 | Engelmann et al. |
| 5,989,194 A | 11/1999 | Davenport et al. |
| 5,989,245 A | 11/1999 | Prescott |
| 5,991,654 A | 11/1999 | Tumey et al. |
| 5,991,694 A | 11/1999 | Gudat et al. |
| 5,993,400 A | 11/1999 | Rincoe et al. |
| 5,997,472 A | 12/1999 | Bonnell et al. |
| 5,999,836 A | 12/1999 | Nelson et al. |
| 5,999,842 A | 12/1999 | Harrison et al. |
| 6,014,346 A | 1/2000 | Malone |
| 6,014,626 A | 1/2000 | Cohen |
| 6,015,387 A | 1/2000 | Schwartz et al. |
| 6,019,729 A | 2/2000 | Itoigawa et al. |
| 6,023,637 A | 2/2000 | Liu et al. |
| 6,025,128 A | 2/2000 | Veltri et al. |
| 6,033,364 A | 3/2000 | Ohman et al. |
| 6,034,526 A | 3/2000 | Montant et al. |
| 6,035,230 A | 3/2000 | Kang et al. |
| 6,047,201 A | 4/2000 | Jackson, III |
| 6,047,203 A | 4/2000 | Sackner et al. |
| 6,056,692 A | 5/2000 | Schwartz |
| 6,063,044 A | 5/2000 | Leonard et al. |
| 6,064,770 A | 5/2000 | Scarth et al. |
| 6,069,696 A | 5/2000 | McQueen et al. |
| 6,071,956 A | 6/2000 | Slepian et al. |
| 6,075,755 A | 6/2000 | Zarchan |
| 6,077,256 A | 6/2000 | Mann |
| 6,081,741 A | 6/2000 | Hollis |
| 6,084,174 A | 7/2000 | Hedengren et al. |
| 6,086,247 A | 7/2000 | von Hollen |
| 6,098,908 A | 8/2000 | Ng |
| 6,117,077 A | 9/2000 | Del Mar et al. |
| 6,117,087 A | 9/2000 | Kamm et al. |
| 6,121,002 A | 9/2000 | Robins |
| 6,124,597 A | 9/2000 | Shehada et al. |
| 6,126,614 A | 10/2000 | Jenkins et al. |
| 6,133,837 A | 10/2000 | Riley |
| 6,137,527 A | 10/2000 | Abdel-Malek et al. |
| 6,139,495 A | 10/2000 | De La Huerga |
| 6,139,499 A | 10/2000 | Wilk |
| 6,146,358 A | 11/2000 | Rowe |
| 6,149,674 A | 11/2000 | Borders |
| 6,152,881 A | 11/2000 | Raines et al. |
| 6,161,041 A | 12/2000 | Stoop et al. |
| 6,165,151 A | 12/2000 | Weiner |
| 6,165,787 A | 12/2000 | Crabtree et al. |
| 6,168,563 B1 | 1/2001 | Brown |
| 6,170,997 B1 | 1/2001 | Glew et al. |
| 6,177,873 B1 | 1/2001 | Cragun |
| 6,179,786 B1 | 1/2001 | Young |
| 6,179,793 B1 | 1/2001 | Rothman et al. |
| 6,186,962 B1 | 2/2001 | Lloyd et al. |
| 6,190,313 B1 | 2/2001 | Hinkle |
| 6,192,143 B1 | 2/2001 | Souluer |
| 6,193,669 B1 | 2/2001 | Degany et al. |
| 6,195,571 B1 | 2/2001 | Osuge |
| 6,196,973 B1 | 3/2001 | Lazenby et al. |
| 6,197,345 B1 | 3/2001 | Porter |
| 6,200,270 B1 | 3/2001 | Biehl et al. |
| 6,206,835 B1 | 3/2001 | Spillman, Jr. et al. |
| 6,210,301 B1 | 4/2001 | Abraham-Fuchs et al. |
| 6,216,066 B1 | 4/2001 | Goebel et al. |
| 6,217,554 B1 | 4/2001 | Green |
| 6,217,846 B1 | 4/2001 | Stuttle |
| 6,219,929 B1 | 4/2001 | Tasker et al. |
| 6,228,034 B1 | 5/2001 | Voss et al. |
| 6,228,049 B1 | 5/2001 | Schroeder et al. |
| 6,231,591 B1 | 5/2001 | Desai |
| 6,233,479 B1 | 5/2001 | Haddad et al. |
| 6,233,487 B1 | 5/2001 | Mika et al. |
| 6,238,349 B1 | 5/2001 | Hickey |
| 6,238,354 B1 | 5/2001 | Alvarez |
| 6,240,582 B1 | 6/2001 | Reinke |
| 6,241,661 B1 | 6/2001 | Schluess et al. |
| 6,246,992 B1 | 6/2001 | Brown |
| 6,258,046 B1 | 7/2001 | Kimball et al. |
| 6,263,243 B1 | 7/2001 | Lang |
| 6,267,728 B1 | 7/2001 | Hayden |
| 6,268,161 B1 | 7/2001 | Han et al. |
| 6,269,376 B1 | 7/2001 | Dhillon et al. |
| 6,270,463 B1 | 8/2001 | Morris, Sr. et al. |
| 6,271,618 B1 | 8/2001 | Hoffmann et al. |
| 6,271,766 B1 | 8/2001 | Didden et al. |
| 6,272,367 B1 | 8/2001 | Chance |
| 6,275,733 B1 | 8/2001 | Park et al. |

| | | | | | | |
|---|---|---|---|---|---|---|
| 6,277,071 B1 | 8/2001 | Hennessy et al. | | 6,507,754 B2 | 1/2003 | Le Van Quyen et al. |
| 6,280,390 B1 | 8/2001 | Akselrod et al. | | 6,509,747 B2 | 1/2003 | Nagai et al. |
| 6,282,441 B1 | 8/2001 | Raymond et al. | | 6,511,477 B2 | 1/2003 | Altman et al. |
| 6,282,448 B1 | 8/2001 | Katz et al. | | 6,513,026 B1 | 1/2003 | Horvitz et al. |
| 6,283,951 B1 | 9/2001 | Flaherty et al. | | 6,514,195 B1 | 2/2003 | Ferek-Petric |
| 6,287,608 B1 | 9/2001 | Levin et al. | | 6,514,226 B1 | 2/2003 | Levin et al. |
| 6,292,685 B1 | 9/2001 | Pompei | | 6,518,016 B1 | 2/2003 | Bertina et al. |
| 6,299,347 B1 | 10/2001 | Pompei | | 6,520,919 B1 | 2/2003 | Nunome et al. |
| 6,300,085 B1 | 10/2001 | Alkon | | 6,525,712 B1 | 2/2003 | Held |
| 6,304,775 B1 | 10/2001 | Iasemidis et al. | | 6,529,757 B1 | 3/2003 | Patel et al. |
| 6,305,377 B1 | 10/2001 | Portwood et al. | | 6,529,759 B1 | 3/2003 | Tucker et al. |
| 6,312,378 B1 | 11/2001 | Bardy | | 6,533,724 B2 | 3/2003 | McNair |
| 6,317,731 B1 | 11/2001 | Luciano | | 6,536,949 B1 | 3/2003 | Heuser |
| 6,322,548 B1 | 11/2001 | Payne et al. | | 6,537,228 B1 | 3/2003 | Lambert |
| 6,332,502 B1 | 12/2001 | Mills et al. | | 6,539,302 B1 | 3/2003 | Bender et al. |
| 6,336,900 B1 | 1/2002 | Alleckson et al. | | 6,540,668 B1 | 4/2003 | Schulz et al. |
| 6,336,903 B1 | 1/2002 | Bardy | | 6,542,767 B1 | 4/2003 | McNichols et al. |
| 6,338,719 B1 | 1/2002 | Drzewiecki et al. | | 6,544,186 B1 | 4/2003 | Shelby et al. |
| 6,340,928 B1 | 1/2002 | McCurdy | | 6,544,202 B2 | 4/2003 | McEwen et al. |
| 6,352,502 B1 | 3/2002 | Chaiken et al. | | 6,545,603 B1 | 4/2003 | Launay et al. |
| 6,354,999 B1 | 3/2002 | Dgany et al. | | 6,547,736 B1 | 4/2003 | Moehring et al. |
| 6,355,000 B1 | 3/2002 | Ogura | | 6,547,746 B1 | 4/2003 | Marino |
| 6,358,201 B1 | 3/2002 | Childre et al. | | 6,547,749 B2 | 4/2003 | Hansen |
| 6,361,495 B1 | 3/2002 | Grolman | | 6,551,306 B1 | 4/2003 | Carriazo |
| 6,363,270 B1 | 3/2002 | Colla et al. | | 6,552,531 B1 | 4/2003 | Fey et al. |
| 6,377,834 B1 | 4/2002 | Zhou et al. | | 6,554,819 B2 | 4/2003 | Reich |
| 6,382,568 B1 | 5/2002 | Snell | | 6,559,769 B2 | 5/2003 | Anthony et al. |
| 6,383,136 B1 | 5/2002 | Jordan | | 6,560,804 B2 | 5/2003 | Wise et al. |
| 6,383,137 B1 | 5/2002 | Berry | | 6,561,996 B1 | 5/2003 | Gorsuch |
| 6,384,627 B1 | 5/2002 | Fross et al. | | 6,567,705 B1 | 5/2003 | Stokes et al. |
| 6,385,332 B1 | 5/2002 | Zahalka et al. | | 6,569,095 B2 | 5/2003 | Eggers |
| 6,387,048 B1 | 5/2002 | Schulman et al. | | 6,573,063 B2 | 6/2003 | Hochman |
| 6,387,059 B1 | 5/2002 | Marchitto et al. | | 6,577,901 B2 | 6/2003 | Thompson |
| 6,393,315 B1 | 5/2002 | Aprahamian et al. | | 6,580,994 B2 | 6/2003 | Katayama et al. |
| 6,402,371 B2 | 6/2002 | Pompei et al. | | 6,582,379 B1 | 6/2003 | Stisen |
| 6,409,662 B1 | 6/2002 | Lloyd et al. | | 6,583,411 B1 | 6/2003 | Altmann et al. |
| 6,413,223 B1 | 7/2002 | Yang et al. | | 6,584,345 B2 | 6/2003 | Govari |
| 6,413,233 B1 | 7/2002 | Sites et al. | | 6,584,628 B1 | 7/2003 | Kummer et al. |
| 6,416,471 B1 | 7/2002 | Kumar et al. | | 6,584,931 B1 | 7/2003 | Kall et al. |
| 6,425,875 B1 | 7/2002 | Reifman et al. | | 6,585,328 B1 | 7/2003 | Oexman et al. |
| 6,430,430 B1 | 8/2002 | Gosche | | 6,585,763 B1 | 7/2003 | Keilman et al. |
| 6,438,216 B1 | 8/2002 | Aktas | | 6,591,182 B1 | 7/2003 | Cece et al. |
| 6,440,067 B1 | 8/2002 | DeLuca et al. | | 6,592,567 B1 | 7/2003 | Levin et al. |
| 6,440,084 B1 | 8/2002 | Gentempo et al. | | 6,594,518 B1 | 7/2003 | Benaron et al. |
| 6,440,090 B1 | 8/2002 | Schallhorn | | 6,597,940 B2 | 7/2003 | Bishop et al. |
| 6,442,241 B1 | 8/2002 | Tsumpes | | 6,597,948 B1 | 7/2003 | Rockwell et al. |
| 6,442,421 B1 | 8/2002 | Le Van Quyen et al. | | 6,600,425 B1 | 7/2003 | Parsadayan |
| 6,445,183 B1 | 9/2002 | Shimizu et al. | | 6,600,949 B1 | 7/2003 | Turcott |
| 6,445,945 B1 | 9/2002 | Arsenault | | 6,604,650 B2 | 8/2003 | Sagar |
| 6,447,455 B2 | 9/2002 | Bang et al. | | 6,606,579 B1 | 8/2003 | Gu |
| 6,447,460 B1 | 9/2002 | Zheng et al. | | 6,610,024 B1 | 8/2003 | Benatti |
| 6,450,027 B1 | 9/2002 | Hogfors et al. | | 6,611,846 B1 | 8/2003 | Stoodley |
| 6,454,705 B1 | 9/2002 | Cosentino et al. | | 6,612,982 B1 | 9/2003 | Ouchi |
| 6,454,718 B1 | 9/2002 | Clift | | 6,615,071 B1 | 9/2003 | Casscells, III et al. |
| 6,455,243 B1 | 9/2002 | Jeejeebhoy | | 6,616,606 B1 | 9/2003 | Petersen et al. |
| 6,458,150 B1 | 10/2002 | Evans et al. | | 6,616,611 B1 | 9/2003 | Moehring |
| 6,459,929 B1 | 10/2002 | Hopper et al. | | 6,616,613 B1 | 9/2003 | Goodman |
| 6,461,303 B2 | 10/2002 | Angelsen | | 6,620,115 B2 | 9/2003 | Sarvazyan et al. |
| 6,463,310 B1 | 10/2002 | Swedlow et al. | | 6,620,146 B2 | 9/2003 | Gibbs |
| 6,464,646 B1 | 10/2002 | Shalom et al. | | 6,621,506 B2 | 9/2003 | Burbidge |
| 6,468,242 B1 | 10/2002 | Wilson et al. | | 6,621,918 B1 | 9/2003 | Hu et al. |
| 6,473,708 B1 | 10/2002 | Watkins et al. | | 6,625,252 B2 | 9/2003 | Mirabella |
| 6,475,155 B2 | 11/2002 | Ogura et al. | | 6,626,840 B2 | 9/2003 | Drzewiecki et al. |
| 6,475,159 B1 | 11/2002 | Casscells et al. | | 6,629,937 B2 | 10/2003 | Watrous |
| 6,475,170 B1 | 11/2002 | Doron et al. | | 6,631,287 B2 | 10/2003 | Newman et al. |
| 6,478,737 B2 | 11/2002 | Bardy | | 6,635,017 B1 | 10/2003 | Moehring et al. |
| 6,478,757 B1 | 11/2002 | Barak | | 6,635,027 B1 | 10/2003 | Cragg et al. |
| 6,482,197 B2 | 11/2002 | Finch et al. | | 6,635,049 B1 | 10/2003 | Robinson et al. |
| 6,484,047 B1 | 11/2002 | Vilsmeier | | 6,636,621 B2 | 10/2003 | Thebaud |
| 6,485,416 B1 | 11/2002 | Platt et al. | | 6,636,755 B2 | 10/2003 | Toida |
| 6,487,507 B1 | 11/2002 | Mansfield et al. | | 6,638,218 B2 | 10/2003 | Bulat |
| 6,490,490 B1 | 12/2002 | Uchikubo et al. | | 6,641,533 B2 | 11/2003 | Causey, III et al. |
| 6,497,222 B2 | 12/2002 | Bolz et al. | | 6,643,646 B2 | 11/2003 | Su et al. |
| 6,501,849 B1 | 12/2002 | Gupta et al. | | 6,645,165 B2 | 11/2003 | Waldridge et al. |
| 6,505,196 B2 | 1/2003 | Drucker et al. | | 6,645,192 B2 | 11/2003 | Kenison et al. |
| 6,506,153 B1 | 1/2003 | Littek et al. | | 6,646,556 B1 | 11/2003 | Smith et al. |
| 6,506,437 B1 | 1/2003 | Harish et al. | | 6,647,093 B2 | 11/2003 | Schmitz et al. |
| 6,507,663 B2 | 1/2003 | Souluer | | 6,652,465 B2 | 11/2003 | Ogura |
| 6,507,747 B1 | 1/2003 | Gowda et al. | | 6,658,292 B2 | 12/2003 | Kroll et al. |

| Patent | Date | Name |
|---|---|---|
| 6,659,327 B2 | 12/2003 | Heck et al. |
| 6,660,028 B2 | 12/2003 | Magers et al. |
| 6,663,242 B1 | 12/2003 | Davenport |
| 6,668,188 B2 | 12/2003 | Sun et al. |
| 6,671,529 B2 | 12/2003 | Claure et al. |
| 6,671,540 B1 | 12/2003 | Hochman |
| 6,671,541 B2 | 12/2003 | Bishop et al. |
| 6,671,547 B2 | 12/2003 | Lyster et al. |
| 6,672,307 B2 | 1/2004 | McDonald et al. |
| 6,673,561 B1 | 1/2004 | Morris |
| 6,675,040 B1 | 1/2004 | Cosman |
| 6,676,608 B1 | 1/2004 | Keren |
| 6,679,830 B2 | 1/2004 | Kolarovic et al. |
| 6,682,483 B1 | 1/2004 | Abend et al. |
| 6,682,490 B2 | 1/2004 | Roy et al. |
| 6,685,303 B1 | 2/2004 | Trauernicht et al. |
| 6,687,230 B1 | 2/2004 | Furutono et al. |
| 6,687,544 B1 | 2/2004 | Levine et al. |
| 6,689,069 B2 | 2/2004 | Bratteli et al. |
| 6,689,612 B2 | 2/2004 | Samsoondar |
| 6,689,974 B2 | 2/2004 | Guillot et al. |
| 6,690,267 B2 | 2/2004 | Linden et al. |
| 6,691,979 B2 | 2/2004 | Parsons et al. |
| 6,694,176 B1 | 2/2004 | Tsujita et al. |
| 6,694,177 B2 | 2/2004 | Eggers et al. |
| 6,699,231 B1 | 3/2004 | Sterman et al. |
| 6,706,001 B2 | 3/2004 | Fresco |
| 6,709,444 B1 | 3/2004 | Makower |
| 6,711,436 B1 | 3/2004 | Duhaylongsod |
| 6,715,402 B2 | 4/2004 | Pfaff et al. |
| 6,717,337 B2 | 4/2004 | Howarth et al. |
| 6,720,712 B2 | 4/2004 | Scott et al. |
| 6,720,875 B2 | 4/2004 | Philippe |
| 6,721,980 B1 | 4/2004 | Price et al. |
| 6,731,976 B2 | 5/2004 | Penn et al. |
| 6,732,884 B2 | 5/2004 | Topliffe et al. |
| 6,733,447 B2 | 5/2004 | Lai et al. |
| 6,733,461 B2 | 5/2004 | Bratteli |
| 6,735,331 B1 | 5/2004 | Binnun et al. |
| 6,736,790 B2 | 5/2004 | Barbut et al. |
| 6,738,655 B1 | 5/2004 | Sen et al. |
| 6,738,769 B2 | 5/2004 | Sharp |
| 6,740,042 B1 | 5/2004 | Lerner et al. |
| 6,740,045 B2 | 5/2004 | Amano |
| 6,740,076 B2 | 5/2004 | Hoben et al. |
| 6,748,929 B2 | 6/2004 | Przymusinski et al. |
| 6,749,619 B2 | 6/2004 | Ouriel et al. |
| 6,751,255 B1 | 6/2004 | Reuven et al. |
| 6,752,771 B2 | 6/2004 | Rothman et al. |
| 6,755,783 B2 | 6/2004 | Cosentino et al. |
| 6,757,412 B1 | 6/2004 | Parsons et al. |
| 6,763,261 B2 | 7/2004 | Casscells, III et al. |
| 6,763,262 B2 | 7/2004 | Hohla et al. |
| 6,770,045 B2 | 8/2004 | Naft et al. |
| 6,773,404 B2 | 8/2004 | Poezevera et al. |
| 6,776,756 B2 | 8/2004 | Feldon et al. |
| 6,783,492 B2 | 8/2004 | Dominguez et al. |
| 6,785,358 B2 | 8/2004 | Johnson et al. |
| 6,786,879 B1 | 9/2004 | Bolam et al. |
| 6,790,204 B2 | 9/2004 | Zadno-Azizi et al. |
| 6,791,460 B2 | 9/2004 | Dixon et al. |
| 6,793,625 B2 | 9/2004 | Cavallaro et al. |
| 6,798,226 B2 | 9/2004 | Altmann et al. |
| 6,801,137 B2 | 10/2004 | Eggers |
| 6,802,811 B1 | 10/2004 | Slepian |
| 6,804,654 B2 | 10/2004 | Kobylevsky et al. |
| 6,809,653 B1 | 10/2004 | Mann et al. |
| 6,810,876 B2 | 11/2004 | Berthon-Jones |
| 6,813,009 B2 | 11/2004 | Riordan et al. |
| 6,816,743 B2 | 11/2004 | Moreno et al. |
| 6,816,744 B2 | 11/2004 | Garfield et al. |
| 6,822,564 B2 | 11/2004 | Al-Ali |
| 6,822,571 B2 | 11/2004 | Conway |
| 6,824,512 B2 | 11/2004 | Warkentin et al. |
| 6,826,578 B2 | 11/2004 | Brackett et al. |
| 6,830,549 B2 | 12/2004 | Bui et al. |
| 6,830,577 B2 | 12/2004 | Nash et al. |
| 6,834,306 B1 | 12/2004 | Tsimelzon |
| 6,835,351 B2 | 12/2004 | Huber et al. |
| 6,835,553 B2 | 12/2004 | Han et al. |
| 6,836,528 B2 | 12/2004 | Reddy et al. |
| 6,837,351 B2 | 1/2005 | Showalter et al. |
| 6,839,455 B2 | 1/2005 | Kaufman |
| 6,840,117 B2 | 1/2005 | Hubbard, Jr. |
| 6,843,772 B2 | 1/2005 | Nunome et al. |
| 6,843,774 B2 | 1/2005 | Foust et al. |
| 6,845,146 B2 | 1/2005 | Rick et al. |
| 6,847,841 B1 | 1/2005 | El Hatw |
| 6,847,913 B2 | 1/2005 | Wigley et al. |
| 6,852,132 B1 | 2/2005 | Houser et al. |
| 6,854,459 B1 | 2/2005 | Cox |
| 6,856,831 B2 | 2/2005 | Griffin et al. |
| 6,871,214 B2 | 3/2005 | Parsons et al. |
| 6,878,111 B2 | 4/2005 | Kenknight et al. |
| 6,878,117 B1 | 4/2005 | Watrous |
| 6,878,518 B2 | 4/2005 | Whitehead |
| 6,880,387 B2 | 4/2005 | Kessler et al. |
| 6,881,192 B1 | 4/2005 | Park |
| 6,885,882 B2 | 4/2005 | Cote et al. |
| 6,886,002 B2 | 4/2005 | Horvitz |
| 6,886,200 B2 | 5/2005 | Blyshak et al. |
| 6,887,201 B2 | 5/2005 | Bardy |
| 6,892,405 B1 | 5/2005 | Dimitriu et al. |
| 6,893,089 B2 | 5/2005 | McMillen et al. |
| 6,893,396 B2 | 5/2005 | Schulze et al. |
| 6,895,265 B2 | 5/2005 | Silver |
| 6,898,457 B1 | 5/2005 | Kraus et al. |
| 6,898,585 B2 | 5/2005 | Benson et al. |
| 6,902,576 B2 | 6/2005 | Drasler et al. |
| 6,905,505 B2 | 6/2005 | Nash et al. |
| 6,907,375 B2 | 6/2005 | Guggari et al. |
| 6,908,431 B2 | 6/2005 | Bardy |
| 6,908,437 B2 | 6/2005 | Bardy |
| 6,916,424 B2 | 7/2005 | Collins et al. |
| 6,921,365 B2 | 7/2005 | Lee |
| 6,922,592 B2 | 7/2005 | Thompson et al. |
| 6,923,771 B2 | 8/2005 | Ogura et al. |
| 6,925,621 B2 | 8/2005 | Mielke et al. |
| 6,926,668 B2 | 8/2005 | Bardy |
| 6,929,922 B1 | 8/2005 | Connor et al. |
| 6,932,091 B2 | 8/2005 | Frazier et al. |
| 6,934,579 B2 | 8/2005 | Mantzaridis et al. |
| 6,936,025 B1 | 8/2005 | Evans et al. |
| 6,939,304 B2 | 9/2005 | Schnall et al. |
| 6,939,322 B2 | 9/2005 | Crank et al. |
| 6,942,616 B2 | 9/2005 | Kerr, III |
| 6,942,626 B2 | 9/2005 | Salisbury et al. |
| 6,943,574 B2 | 9/2005 | Altmann et al. |
| 6,944,497 B2 | 9/2005 | Stypulkowski |
| 6,945,944 B2 | 9/2005 | Kuiper et al. |
| 6,947,780 B2 | 9/2005 | Scharf |
| 6,947,781 B2 | 9/2005 | Asada et al. |
| 6,949,075 B2 | 9/2005 | Hatlesad et al. |
| 6,950,692 B2 | 9/2005 | Gelikonov et al. |
| 6,950,693 B1 | 9/2005 | Wehberg |
| 6,953,666 B1 | 10/2005 | Kinkade, Jr. et al. |
| 6,955,113 B2 | 10/2005 | Demers |
| 6,959,211 B2 | 10/2005 | Rule et al. |
| 6,961,327 B2 | 11/2005 | Niu |
| 6,961,971 B2 | 11/2005 | Schneider et al. |
| 6,963,772 B2 | 11/2005 | Bloom et al. |
| 6,966,557 B2 | 11/2005 | Kirk et al. |
| 6,966,650 B2 | 11/2005 | Hu et al. |
| 6,968,294 B2 | 11/2005 | Gutta et al. |
| 6,968,375 B1 | 11/2005 | Brown |
| 6,969,345 B2 | 11/2005 | Jassawalla et al. |
| 6,969,355 B2 | 11/2005 | Narimatsu |
| 6,970,737 B1 | 11/2005 | Brodnick et al. |
| 6,970,847 B1 | 11/2005 | Melen et al. |
| 6,972,122 B2 | 12/2005 | Haroon et al. |
| 6,974,463 B2 | 12/2005 | Magers et al. |
| 6,974,567 B2 | 12/2005 | Edwards et al. |
| 6,975,232 B1 | 12/2005 | McKenna |
| 6,975,898 B2 | 12/2005 | Seibel |
| 6,978,169 B1 | 12/2005 | Guerra |
| 6,978,182 B2 | 12/2005 | Mazar et al. |
| 6,979,293 B2 | 12/2005 | Hansmann et al. |
| 6,979,296 B2 | 12/2005 | See |

| Patent | Type | Date | Inventor |
|---|---|---|---|
| 6,980,851 | B2 | 12/2005 | Zhu et al. |
| 6,980,852 | B2 | 12/2005 | Jersey-Willuhn et al. |
| 6,983,178 | B2 | 1/2006 | Fine et al. |
| 6,984,207 | B1 | 1/2006 | Sullivan et al. |
| 6,984,373 | B2 | 1/2006 | Wescott et al. |
| 6,988,088 | B1 | 1/2006 | Miikkulainen et al. |
| 6,988,499 | B2 | 1/2006 | Holt et al. |
| 6,990,365 | B1 | 1/2006 | Parker et al. |
| 6,990,371 | B2 | 1/2006 | Powers et al. |
| 6,990,455 | B2 | 1/2006 | Vozick et al. |
| 6,990,980 | B2 | 1/2006 | Richey, II |
| 6,993,167 | B1 | 1/2006 | Skladnev et al. |
| 6,993,380 | B1 | 1/2006 | Modarres |
| 6,993,382 | B2 | 1/2006 | Casscells et al. |
| 6,996,427 | B2 | 2/2006 | Ali et al. |
| 6,999,812 | B2 | 2/2006 | Kawada et al. |
| 7,001,338 | B2 | 2/2006 | Hayek et al. |
| 7,003,340 | B2 | 2/2006 | Say et al. |
| 7,003,525 | B1 | 2/2006 | Horvitz et al. |
| 7,004,907 | B2 | 2/2006 | Banet et al. |
| 7,004,911 | B1 | 2/2006 | Tu et al. |
| 7,006,676 | B1 | 2/2006 | Zeylikovich et al. |
| 7,006,858 | B2 | 2/2006 | Silver et al. |
| 7,006,861 | B2 | 2/2006 | Flock et al. |
| 7,011,633 | B2 | 3/2006 | Strandberg |
| 7,011,645 | B2 | 3/2006 | McGuckin, Jr. et al. |
| 7,014,861 | B2 | 3/2006 | Roorda et al. |
| 7,016,021 | B2 | 3/2006 | Nakajima et al. |
| 7,016,467 | B2 | 3/2006 | Brooks |
| 7,016,601 | B1 | 3/2006 | Yoneya et al. |
| 7,020,666 | B2 | 3/2006 | Doise et al. |
| 7,024,234 | B2 | 4/2006 | Margulies et al. |
| 7,025,778 | B2 | 4/2006 | Hayashi et al. |
| 7,027,871 | B2 | 4/2006 | Burnes et al. |
| 7,029,447 | B2 | 4/2006 | Rantala |
| 7,030,764 | B2 | 4/2006 | Smith et al. |
| 7,033,776 | B2 | 4/2006 | Toombs |
| 7,035,684 | B2 | 4/2006 | Lee |
| 7,037,256 | B2 | 5/2006 | Osbon et al. |
| 7,037,273 | B2 | 5/2006 | Zhu et al. |
| 7,038,595 | B2 | 5/2006 | Seely |
| 7,039,698 | B2 | 5/2006 | Slemmer et al. |
| 7,041,079 | B2 | 5/2006 | Yozu et al. |
| 7,043,288 | B2 | 5/2006 | Davis, III et al. |
| 7,047,083 | B2 | 5/2006 | Gunderson et al. |
| 7,047,149 | B1 | 5/2006 | Maki et al. |
| 7,051,738 | B2 | 5/2006 | Oron et al. |
| 7,052,427 | B2 | 5/2006 | Kapaan et al. |
| 7,052,474 | B2 | 5/2006 | Castell et al. |
| 7,058,450 | B2 | 6/2006 | Struble et al. |
| 7,062,528 | B2 | 6/2006 | Deguchi |
| 7,065,465 | B2 | 6/2006 | Chen et al. |
| 7,066,873 | B2 | 6/2006 | Hughett et al. |
| 7,069,086 | B2 | 6/2006 | Von Arx |
| 7,072,711 | B2 | 7/2006 | Girouard et al. |
| 7,074,188 | B2 | 7/2006 | Nair et al. |
| 7,074,426 | B2 | 7/2006 | Kochinke |
| 7,076,436 | B1 | 7/2006 | Ross, Jr. et al. |
| 7,077,809 | B2 | 7/2006 | Wu et al. |
| 7,079,035 | B2 | 7/2006 | Bock et al. |
| 7,087,395 | B1 | 8/2006 | Garrity et al. |
| 7,087,903 | B2 | 8/2006 | Balan et al. |
| 7,088,993 | B2 | 8/2006 | Dumont et al. |
| 7,092,970 | B2 | 8/2006 | Shiibashi et al. |
| 7,097,625 | B2 | 8/2006 | Steinberg |
| 7,098,673 | B2 | 8/2006 | Launay et al. |
| 7,098,678 | B2 | 8/2006 | Altmann et al. |
| 7,100,491 | B2 | 9/2006 | Yatsko et al. |
| 7,104,955 | B2 | 9/2006 | Bardy |
| 7,107,096 | B2 | 9/2006 | Fischell et al. |
| 7,108,686 | B2 | 9/2006 | Burke et al. |
| 7,110,806 | B2 | 9/2006 | Prince |
| 7,112,318 | B2 | 9/2006 | Madar et al. |
| 7,113,819 | B2 | 9/2006 | Hamilton et al. |
| 7,115,097 | B2 | 10/2006 | Johnson |
| 7,116,655 | B2 | 10/2006 | Yegoshin |
| 7,116,825 | B2 | 10/2006 | Lee et al. |
| 7,117,036 | B2 | 10/2006 | Florio |
| 7,117,037 | B2 | 10/2006 | Hiebert et al. |
| 7,122,005 | B2 | 10/2006 | Shusterman |
| 7,122,019 | B1 | 10/2006 | Kesten et al. |
| 7,123,950 | B2 | 10/2006 | Mannheimer |
| 7,124,837 | B2 | 10/2006 | Martin et al. |
| 7,127,370 | B2 | 10/2006 | Kelly, Jr. et al. |
| 7,128,713 | B2 | 10/2006 | Moehring et al. |
| 7,130,396 | B2 | 10/2006 | Rogers et al. |
| 7,133,661 | B2 | 11/2006 | Hatae et al. |
| 7,134,157 | B2 | 11/2006 | Koch |
| 7,135,007 | B2 | 11/2006 | Scott et al. |
| 7,135,032 | B2 | 11/2006 | Akerfeldt |
| 7,136,357 | B2 | 11/2006 | Soumiya et al. |
| 7,136,704 | B2 | 11/2006 | Schulman |
| 7,138,902 | B2 | 11/2006 | Menard |
| 7,142,632 | B2 | 11/2006 | Atzinger et al. |
| 7,143,222 | B2 | 11/2006 | Fisher et al. |
| 7,144,099 | B2 | 12/2006 | Cabal et al. |
| 7,146,664 | B1 | 12/2006 | Grosvenor |
| 7,147,600 | B2 | 12/2006 | Bardy |
| 7,149,645 | B2 | 12/2006 | Mangrulkar et al. |
| 7,151,957 | B2 | 12/2006 | Beker et al. |
| 7,155,273 | B2 | 12/2006 | Taylor |
| 7,155,281 | B1 | 12/2006 | Fayram |
| 7,155,729 | B1 | 12/2006 | Andrew et al. |
| 7,158,692 | B2 | 1/2007 | Chalana et al. |
| 7,158,861 | B2 | 1/2007 | Wang et al. |
| 7,162,061 | B1 | 1/2007 | Takeo |
| 7,162,062 | B2 | 1/2007 | Breitenstein et al. |
| 7,162,068 | B2 | 1/2007 | Akagi |
| 7,163,520 | B2 | 1/2007 | Bernard et al. |
| 7,164,941 | B2 | 1/2007 | Misczynski et al. |
| 7,164,948 | B2 | 1/2007 | Struble et al. |
| 7,167,734 | B2 | 1/2007 | Khalil et al. |
| 7,171,251 | B2 | 1/2007 | Sarussi et al. |
| 7,171,680 | B2 | 1/2007 | Lange |
| 7,172,493 | B2 | 2/2007 | Novak et al. |
| 7,174,005 | B1 | 2/2007 | Rodkey et al. |
| 7,177,699 | B2 | 2/2007 | Fabian et al. |
| 7,179,251 | B2 | 2/2007 | Palasis |
| 7,180,415 | B2 | 2/2007 | Bankert et al. |
| 7,180,983 | B2 | 2/2007 | Uchida et al. |
| 7,181,054 | B2 | 2/2007 | Zaleski |
| 7,183,057 | B2 | 2/2007 | Benson |
| 7,184,580 | B2 | 2/2007 | Hamid |
| 7,184,820 | B2 | 2/2007 | Jersey-Willuhn et al. |
| 6,580,016 | C1 | 3/2007 | Teirstein et al. |
| 7,187,960 | B2 | 3/2007 | Abreu |
| 7,189,204 | B2 | 3/2007 | Ni et al. |
| 7,190,987 | B2 | 3/2007 | Lindekugel et al. |
| 7,190,996 | B2 | 3/2007 | Jarverud |
| 7,191,018 | B2 | 3/2007 | Gielen et al. |
| 7,192,726 | B1 | 3/2007 | Carr, Jr. et al. |
| 7,195,598 | B2 | 3/2007 | Fuchs et al. |
| 7,195,640 | B2 | 3/2007 | Falotico et al. |
| 7,196,620 | B2 | 3/2007 | Nanba |
| 7,198,603 | B2 | 4/2007 | Penner et al. |
| 7,199,494 | B2 | 4/2007 | Rapp et al. |
| 7,200,431 | B2 | 4/2007 | Franco et al. |
| 7,200,682 | B2 | 4/2007 | Miyazaki et al. |
| 7,202,844 | B2 | 4/2007 | Nakamigawa |
| 7,203,294 | B2 | 4/2007 | Carnazza et al. |
| 7,205,991 | B2 | 4/2007 | Fitzmaurice et al. |
| 7,207,939 | B2 | 4/2007 | Husher |
| 7,208,983 | B2 | 4/2007 | Imaizumi et al. |
| 7,209,671 | B1 | 4/2007 | Hayee et al. |
| 7,209,955 | B1 | 4/2007 | Major et al. |
| 7,211,048 | B1 | 5/2007 | Najafi et |
| 7,211,063 | B2 | 5/2007 | Tom |
| 7,212,111 | B2 | 5/2007 | Tupler et al. |
| 7,213,009 | B2 | 5/2007 | Pestonik et al. |
| 7,214,094 | B2 | 5/2007 | Kaminski et al. |
| 7,214,191 | B2 | 5/2007 | Stringer et al. |
| 7,214,193 | B2 | 5/2007 | Freund et al. |
| 7,214,194 | B2 | 5/2007 | Klyukin |
| 7,214,195 | B2 | 5/2007 | Mitra |
| 7,214,202 | B1 | 5/2007 | Vogel et al. |
| 7,216,263 | B2 | 5/2007 | Takaoka et al. |
| 7,217,735 | B1 | 5/2007 | Au et al. |
| 7,218,966 | B2 | 5/2007 | Haefner |

| | | |
|---|---|---|
| 7,224,281 B2 | 5/2007 | Santoso et al. |
| 7,225,005 B2 | 5/2007 | Kaufman et al. |
| 7,225,013 B2 | 5/2007 | Geva et al. |
| 7,226,415 B2 | 6/2007 | Haddad et al. |
| 7,226,419 B2 | 6/2007 | Lane et al. |
| 7,226,422 B2 | 6/2007 | Hatlestad et al. |
| 7,226,426 B2 | 6/2007 | Thomson |
| 7,228,315 B2 | 6/2007 | Finitzo et al. |
| 7,231,258 B2 | 6/2007 | Moore et al. |
| 7,232,158 B2 | 6/2007 | Wilkendorf |
| 7,232,415 B2 | 6/2007 | Steinberg |
| 7,233,781 B2 | 6/2007 | Hunter et al. |
| 7,234,359 B2 | 6/2007 | Hirose et al. |
| 7,236,815 B2 | 6/2007 | Richards-Kortum et al. |
| 7,238,158 B2 | 7/2007 | Abend |
| 7,241,273 B2 | 7/2007 | Maguire et al. |
| 7,242,807 B2 | 7/2007 | Waupotitsch et al. |
| 7,244,122 B2 | 7/2007 | Jung et al. |
| 7,248,733 B2 | 7/2007 | Ohta |
| 7,248,916 B2 | 7/2007 | Bardy |
| 7,248,917 B2 | 7/2007 | den Boer |
| 7,248,921 B2 | 7/2007 | Palreddy et al. |
| 7,250,855 B2 | 7/2007 | Suenbuel et al. |
| 7,252,637 B2 | 8/2007 | Ebner et al. |
| 7,252,640 B2 | 8/2007 | Ni et al. |
| 7,254,425 B2 | 8/2007 | Lowery et al. |
| 7,254,430 B2 | 8/2007 | Cho et al. |
| 7,254,432 B2 | 8/2007 | Fine |
| 7,257,531 B2 | 8/2007 | Holub |
| 7,258,666 B2 | 8/2007 | Brown |
| 7,258,670 B2 | 8/2007 | Bardy |
| 7,260,064 B2 | 8/2007 | Basu et al. |
| 7,260,440 B2 | 8/2007 | Selim et al. |
| 7,261,690 B2 | 8/2007 | Teller et al. |
| 7,261,735 B2 | 8/2007 | Lianos et al. |
| 7,263,073 B2 | 8/2007 | Petite et al. |
| 7,263,688 B2 | 8/2007 | Pitzel et al. |
| 7,264,591 B2 | 9/2007 | Brown |
| 7,265,676 B2 | 9/2007 | Gordon et al. |
| 7,269,476 B2 | 9/2007 | Ratnakar |
| 7,269,483 B2 | 9/2007 | Schubert et al. |
| 7,269,484 B2 | 9/2007 | Hein |
| 7,269,718 B2 | 9/2007 | Alexander, III et al. |
| 7,270,374 B2 | 9/2007 | Moriggi |
| 7,272,435 B2 | 9/2007 | Rowlandson |
| 7,273,053 B2 | 9/2007 | Zocca et al. |
| 7,275,829 B2 | 10/2007 | Sugiura et al. |
| 7,275,867 B2 | 10/2007 | Lee |
| 7,276,031 B2 | 10/2007 | Norman et al. |
| 7,277,747 B2 | 10/2007 | Cazares et al. |
| 7,277,903 B2 | 10/2007 | Petrocelli |
| 7,278,179 B2 | 10/2007 | Schneider |
| 7,280,858 B2 | 10/2007 | Al-Ali et al. |
| 7,280,992 B2 | 10/2007 | Nitz |
| 7,283,153 B2 | 10/2007 | Provost et al. |
| 7,284,061 B2 | 10/2007 | Matsubayashi et al. |
| 7,285,090 B2 | 10/2007 | Stivoric et al. |
| 7,286,648 B1 | 10/2007 | Chang et al. |
| 7,286,872 B2 | 10/2007 | Kramer et al. |
| 7,286,877 B2 | 10/2007 | Daum |
| 7,289,029 B2 | 10/2007 | Medema et al. |
| 7,289,253 B2 | 10/2007 | Thomas |
| 7,289,883 B2 | 10/2007 | Wang et al. |
| 7,289,927 B2 | 10/2007 | Bedard et al. |
| 7,291,111 B2 | 11/2007 | Shertukde et al. |
| 7,291,497 B2 | 11/2007 | Holmes et al. |
| 7,292,719 B2 | 11/2007 | Arnon |
| 7,294,108 B1 | 11/2007 | Bornzin et al. |
| 7,296,042 B2 | 11/2007 | Edwards et al. |
| 7,296,238 B1 | 11/2007 | Zurawski |
| 7,297,108 B2 | 11/2007 | Iliff |
| 7,297,154 B2 | 11/2007 | Tu et al. |
| 7,297,280 B2 | 11/2007 | Krivitski et al. |
| 7,297,475 B2 | 11/2007 | Koiwai et al. |
| 7,299,085 B2 | 11/2007 | Bergelson et al. |
| 7,299,157 B2 | 11/2007 | Malik |
| 7,300,453 B2 | 11/2007 | Yon |
| 7,300,662 B2 | 11/2007 | Falotico et al. |
| 7,300,754 B2 | 11/2007 | Abi Fadel et al. |
| 7,301,256 B2 | 11/2007 | Marzahn |
| 7,303,555 B2 | 12/2007 | Makin et al. |
| 7,303,575 B2 | 12/2007 | Ogle |
| 7,304,580 B2 | 12/2007 | Sullivan et al. |
| 7,305,262 B2 | 12/2007 | Brodnick et al. |
| 7,306,565 B2 | 12/2007 | Fraden et al. |
| 7,306,953 B2 | 12/2007 | Probert et al. |
| 7,308,246 B2 | 12/2007 | Yamazaki et al. |
| 7,308,292 B2 | 12/2007 | Colvin et al. |
| 7,308,309 B1 | 12/2007 | Koh |
| 7,308,492 B2 | 12/2007 | Konopka et al. |
| 7,310,564 B2 | 12/2007 | Leyerer et al. |
| 7,310,607 B2 | 12/2007 | Brandt et al. |
| 7,310,615 B2 | 12/2007 | Lewis |
| 7,311,665 B2 | 12/2007 | Hawthorne et al. |
| 7,311,727 B2 | 12/2007 | Mazumder et al. |
| 7,312,619 B2 | 12/2007 | Altmann et al. |
| 7,313,529 B2 | 12/2007 | Thompson |
| 7,314,478 B2 | 1/2008 | Hui |
| 7,315,825 B2 | 1/2008 | Rosenfeld et al. |
| 7,317,821 B2 | 1/2008 | Chen et al. |
| 7,318,004 B2 | 1/2008 | Butterfield |
| 7,318,804 B2 | 1/2008 | Weitzel et al. |
| 7,319,386 B2 | 1/2008 | Collins, Jr. et al. |
| 7,319,400 B2 | 1/2008 | Smith et al. |
| 7,319,899 B2 | 1/2008 | Keizer |
| 7,320,030 B2 | 1/2008 | Brown |
| 7,321,862 B2 | 1/2008 | Rosenfeld et al. |
| 7,324,661 B2 | 1/2008 | Kemp et al. |
| 7,325,054 B2 | 1/2008 | Ishimoto |
| 7,325,297 B2 | 2/2008 | Xia |
| 7,327,637 B2 | 2/2008 | Chambers et al. |
| 7,327,861 B2 | 2/2008 | Choshi et al. |
| 7,328,472 B2 | 2/2008 | Chaffee |
| 7,329,236 B2 | 2/2008 | Kesten et al. |
| 7,329,266 B2 | 2/2008 | Royse et al. |
| 7,330,127 B2 | 2/2008 | Price et al. |
| 7,331,667 B2 | 2/2008 | Grotehusmann et al. |
| 7,331,928 B2 | 2/2008 | Seki et al. |
| 7,332,743 B2 | 2/2008 | Yang et al. |
| 7,333,002 B2 | 2/2008 | Bixler et al. |
| 7,333,014 B2 | 2/2008 | Agrawal et al. |
| 7,333,844 B2 | 2/2008 | Jones et al. |
| 7,336,018 B2 | 2/2008 | Augesky |
| 7,336,166 B2 | 2/2008 | Akamatsu |
| 7,336,187 B2 | 2/2008 | Hubbard, Jr. et al. |
| 7,336,202 B2 | 2/2008 | Kawai et al. |
| 7,336,804 B2 | 2/2008 | Steffin |
| 7,337,677 B2 | 3/2008 | Mizohata |
| 7,337,680 B2 | 3/2008 | Kantro |
| 7,338,443 B1 | 3/2008 | Tucker |
| 7,338,482 B2 | 3/2008 | Lockwood et al. |
| 7,339,299 B2 | 3/2008 | Sesita et al. |
| 7,339,587 B2 | 3/2008 | Kropfeld |
| 7,340,077 B2 | 3/2008 | Gokturk et al. |
| 7,340,240 B2 | 3/2008 | McDonald |
| 7,340,293 B2 | 3/2008 | McQuilkin |
| 7,340,337 B2 | 3/2008 | Katrak |
| 7,340,687 B2 | 3/2008 | Sekiguchi et al. |
| 7,340,951 B2 | 3/2008 | Nyce et al. |
| 7,343,305 B2 | 3/2008 | Benn et al. |
| 7,344,518 B2 | 3/2008 | McGuckin, Jr. et al. |
| 7,346,203 B2 | 3/2008 | Turek et al. |
| 7,346,205 B2 | 3/2008 | Walker, Jr. |
| 7,359,747 B2 | 4/2008 | Iwanczyk et al. |
| 7,369,892 B2 | 5/2008 | Ferek-Petric |
| 7,374,540 B2 | 5/2008 | Schnall |
| 7,389,142 B2 | 6/2008 | Holmström |
| 7,531,133 B2 | 5/2009 | Hole et al. |
| 7,603,166 B2 | 10/2009 | Casscells, III et al. |
| 7,623,908 B2 | 11/2009 | Boppart et al. |
| 7,654,997 B2 | 2/2010 | Makower et al. |
| 7,664,548 B2 | 2/2010 | Amurthur et al. |
| 7,666,151 B2 | 2/2010 | Sullivan et al. |
| 7,729,747 B2 | 6/2010 | Stranc et al. |
| 7,740,612 B2 | 6/2010 | Hochman |
| 7,780,623 B2 | 8/2010 | Soltanpour |
| 7,785,258 B2 | 8/2010 | Braig et al. |
| 7,789,830 B2 | 9/2010 | Ishida et al. |

| Patent/Pub No. | Date | Inventor |
|---|---|---|
| 7,828,739 B2 | 11/2010 | Arnold |
| 7,833,239 B2 | 11/2010 | Nash |
| 7,894,874 B2 | 2/2011 | Lynch et al. |
| 7,931,600 B2 | 4/2011 | Hatlestad et al. |
| 8,005,686 B2 | 8/2011 | Smith |
| 8,096,946 B2 | 1/2012 | Burton |
| 8,157,442 B2 | 4/2012 | Van de Velde et al. |
| 2001/0000262 A1 | 4/2001 | McEwen et al. |
| 2001/0031920 A1 | 10/2001 | Kaufman et al. |
| 2001/0044588 A1 | 11/2001 | Mault |
| 2001/0047137 A1 | 11/2001 | Moreno et al. |
| 2002/0016535 A1 | 2/2002 | Martin et al. |
| 2002/0042583 A1 | 4/2002 | Barak et al. |
| 2002/0099286 A1 | 7/2002 | Sandler et al. |
| 2002/0107504 A1 | 8/2002 | Gordon |
| 2002/0128545 A1 | 9/2002 | Steuer et al. |
| 2003/0026798 A1 | 2/2003 | Zimmerman et al. |
| 2003/0050542 A1 | 3/2003 | Reihl et al. |
| 2003/0065536 A1 | 4/2003 | Hansen et al. |
| 2003/0069481 A1 | 4/2003 | Hervy et al. |
| 2003/0139778 A1* | 7/2003 | Fischell et al. ............. 607/3 |
| 2003/0143158 A1 | 7/2003 | Wescott et al. |
| 2003/0149997 A1 | 8/2003 | Hageman |
| 2003/0195401 A1 | 10/2003 | Tian et al. |
| 2003/0208116 A1 | 11/2003 | Liang et al. |
| 2003/0229691 A1 | 12/2003 | Ishimoto |
| 2004/0019278 A1 | 1/2004 | Abend |
| 2004/0024298 A1 | 2/2004 | Marshik-Geurts et al. |
| 2004/0030578 A1 | 2/2004 | Cross et al. |
| 2004/0034284 A1 | 2/2004 | Aversano et al. |
| 2004/0039264 A1 | 2/2004 | Bardy |
| 2004/0039268 A1 | 2/2004 | Barbour et al. |
| 2004/0073146 A1 | 4/2004 | Weintraub et al. |
| 2004/0091933 A1 | 5/2004 | Stoughton et al. |
| 2004/0122354 A1 | 6/2004 | Semba |
| 2004/0133081 A1 | 7/2004 | Teller et al. |
| 2004/0133082 A1 | 7/2004 | Abraham-Fuchs et al. |
| 2004/0138562 A1 | 7/2004 | Makower et al. |
| 2004/0143401 A1 | 7/2004 | Elling |
| 2004/0147837 A1 | 7/2004 | Macaulay et al. |
| 2004/0176668 A1 | 9/2004 | Goldstein |
| 2004/0176700 A1 | 9/2004 | Potter |
| 2004/0186383 A1 | 9/2004 | Rava et al. |
| 2004/0208343 A1 | 10/2004 | Golden et al. |
| 2004/0210208 A1 | 10/2004 | Paul et al. |
| 2004/0219608 A1 | 11/2004 | Der-Balian |
| 2004/0236225 A1 | 11/2004 | Murphy et al. |
| 2004/0249293 A1 | 12/2004 | Sandler et al. |
| 2004/0260346 A1 | 12/2004 | Overall et al. |
| 2004/0265393 A1 | 12/2004 | Unger et al. |
| 2005/0004461 A1 | 1/2005 | Abend |
| 2005/0027184 A1 | 2/2005 | Saldivar et al. |
| 2005/0033154 A1 | 2/2005 | deCharms |
| 2005/0034485 A1 | 2/2005 | Klefstad-Sillonville et al. |
| 2005/0075531 A1 | 4/2005 | Loeb et al. |
| 2005/0085769 A1 | 4/2005 | MacMahon et al. |
| 2005/0090736 A1 | 4/2005 | Sommer |
| 2005/0090748 A1 | 4/2005 | Makower et al. |
| 2005/0096528 A1 | 5/2005 | Fritz et al. |
| 2005/0124969 A1 | 6/2005 | Fitzgerald et al. |
| 2005/0129731 A1 | 6/2005 | Horres et al. |
| 2005/0142210 A1 | 6/2005 | Porter |
| 2005/0148899 A1 | 7/2005 | Walker et al. |
| 2005/0148953 A1 | 7/2005 | Fulton, III |
| 2005/0159690 A1 | 7/2005 | Barak et al. |
| 2005/0165325 A1 | 7/2005 | Hornig |
| 2005/0175665 A1 | 8/2005 | Hunter et al. |
| 2005/0176678 A1 | 8/2005 | Horres et al. |
| 2005/0186245 A1 | 8/2005 | Hunter et al. |
| 2005/0222526 A1 | 10/2005 | Perry et al. |
| 2005/0234393 A1 | 10/2005 | Wood, Jr. |
| 2005/0234398 A1 | 10/2005 | Wood, Jr. |
| 2005/0234399 A1 | 10/2005 | Wood, Jr. |
| 2005/0234440 A1 | 10/2005 | Wood, Jr. |
| 2005/0261726 A1 | 11/2005 | Pile-Spellman |
| 2005/0287134 A1 | 12/2005 | Klein |
| 2006/0010012 A1 | 1/2006 | Franzblau et al. |
| 2006/0047301 A1 | 3/2006 | Ogle |
| 2006/0069425 A1 | 3/2006 | Hillis et al. |
| 2006/0074362 A1 | 4/2006 | Rousso et al. |
| 2006/0079784 A1 | 4/2006 | Shifrin |
| 2006/0089556 A1 | 4/2006 | Bambot et al. |
| 2006/0100530 A1 | 5/2006 | Kliot et al. |
| 2006/0124140 A1 | 6/2006 | Forsell |
| 2006/0127246 A1 | 6/2006 | Forsell |
| 2006/0135940 A1 | 6/2006 | Joshi |
| 2006/0142783 A1 | 6/2006 | Lewis et al. |
| 2006/0149313 A1 | 7/2006 | Arguello et al. |
| 2006/0181791 A1 | 8/2006 | Van Beck et al. |
| 2006/0184280 A1 | 8/2006 | Oddsson et al. |
| 2006/0224225 A1 | 10/2006 | Ransbury et al. |
| 2006/0241521 A1 | 10/2006 | Cohen |
| 2006/0253301 A1 | 11/2006 | Simms et al. |
| 2006/0290516 A1 | 12/2006 | Muehlsteff et al. |
| 2006/0293572 A1 | 12/2006 | Bulat |
| 2007/0010719 A1 | 1/2007 | Huster et al. |
| 2007/0010868 A1 | 1/2007 | Ferren et al. |
| 2007/0016079 A1 | 1/2007 | Freeman et al. |
| 2007/0021458 A1 | 1/2007 | Ishikawa et al. |
| 2007/0021774 A1 | 1/2007 | Hogendijk |
| 2007/0038042 A1 | 2/2007 | Freeman et al. |
| 2007/0043308 A1 | 2/2007 | Lee |
| 2007/0054266 A1 | 3/2007 | Sato et al. |
| 2007/0060811 A1 | 3/2007 | Roberts |
| 2007/0066929 A1 | 3/2007 | Ferren et al. |
| 2007/0078500 A1 | 4/2007 | Ryan et al. |
| 2007/0083090 A1 | 4/2007 | Sterling et al. |
| 2007/0088334 A1 | 4/2007 | Hillis et al. |
| 2007/0100278 A1 | 5/2007 | Frei et al. |
| 2007/0129639 A1 | 6/2007 | Zhang et al. |
| 2007/0142905 A1 | 6/2007 | Hezi-Yamit et al. |
| 2007/0156211 A1 | 7/2007 | Ferren et al. |
| 2007/0161921 A1 | 7/2007 | Rausch |
| 2007/0166707 A1 | 7/2007 | Schadt et al. |
| 2007/0167836 A1 | 7/2007 | Scepanovic et al. |
| 2007/0168024 A1 | 7/2007 | Khairkhahan |
| 2007/0185470 A1 | 8/2007 | Steinbach et al. |
| 2007/0207131 A1 | 9/2007 | Boss, Jr. et al. |
| 2007/0213600 A1 | 9/2007 | John et al. |
| 2007/0213613 A1 | 9/2007 | Ishida et al. |
| 2007/0232930 A1 | 10/2007 | Freeman et al. |
| 2007/0232940 A1 | 10/2007 | Fine et al. |
| 2007/0232958 A1 | 10/2007 | Donofrio et al. |
| 2007/0233019 A1 | 10/2007 | Forsell |
| 2007/0255199 A1 | 11/2007 | Dewey |
| 2008/0004550 A1 | 1/2008 | Einav et al. |
| 2008/0044072 A1 | 2/2008 | Kiraly et al. |
| 2008/0058758 A1 | 3/2008 | Ranchod et al. |
| 2008/0071185 A1 | 3/2008 | Beck et al. |
| 2008/0077019 A1 | 3/2008 | Xiao et al. |
| 2008/0132976 A1 | 6/2008 | Kane et al. |
| 2008/0146970 A1 | 6/2008 | Litman et al. |
| 2008/0161698 A1 | 7/2008 | Sum et al. |
| 2008/0208011 A1 | 8/2008 | Shuler |
| 2008/0221457 A1 | 9/2008 | Zeng et al. |
| 2008/0242952 A1 | 10/2008 | Jung et al. |
| 2008/0262344 A1 | 10/2008 | Brummett |
| 2008/0275393 A1 | 11/2008 | Bonnette et al. |
| 2008/0294019 A1 | 11/2008 | Tran |
| 2008/0300493 A1 | 12/2008 | Gatto et al. |
| 2008/0320098 A1 | 12/2008 | Jung et al. |
| 2009/0012382 A1 | 1/2009 | Dutta et al. |
| 2009/0048577 A1 | 2/2009 | Gillies et al. |
| 2009/0063518 A1 | 3/2009 | Jung et al. |
| 2009/0198129 A1 | 8/2009 | Varghese et al. |
| 2009/0227997 A1 | 9/2009 | Wang et al. |
| 2009/0234672 A1 | 9/2009 | Dicks et al. |
| 2009/0287093 A1 | 11/2009 | Ferren et al. |
| 2009/0287101 A1 | 11/2009 | Ferren et al. |
| 2009/0306484 A1 | 12/2009 | Kurtz et al. |
| 2009/0324608 A1 | 12/2009 | Meyers et al. |
| 2010/0016733 A1 | 1/2010 | Smith et al. |
| 2010/0063365 A1 | 3/2010 | Pisani et al. |
| 2010/0234714 A1 | 9/2010 | Mercier et al. |
| 2010/0268112 A1 | 10/2010 | Short et al. |
| 2011/0068928 A1 | 3/2011 | Riley et al. |
| 2011/0087113 A1 | 4/2011 | Mack et al. |
| 2011/0098546 A1 | 4/2011 | Farazi et al. |

| 2011/0112416 A1 | 5/2011 | Myr |
| 2011/0160549 A1 | 6/2011 | Saroka et al. |
| 2011/0201955 A1 | 8/2011 | Hatlestad et al. |
| 2011/0257577 A1 | 10/2011 | Lane et al. |

FOREIGN PATENT DOCUMENTS

| WO | WO 2005/046482 A1 | 5/2005 |
| WO | WO 2006/109072 A2 | 10/2006 |
| WO | WO 2007/067952 A2 | 6/2007 |
| WO | WO 2007/093804 A2 | 8/2007 |

OTHER PUBLICATIONS

Caceres-Loriga, Fidel Manuel et al.; "Thrombolytic Treatment as First Option in Recurrent Tricuspid Prosthetic Valve Thrombosis and Ebstein's Anomaly"; J. Pharm. Pharmaceut Sci; 2005; pp. 332-334; located at: www.cspsCanada.org.

Das, Moloy et al.; "Is Thrombolysis or Surgery the Best Option for Actue Prosthetic Valve Thrombosis?"; Interactive CardioVascular and Thoracic Surgery; 2007; pp. 806-812; vol. 6; located at: www.icvts.ctsnetjournals.org.

Kasai, Chihiro et al.; "Real-Time Two-Dimensional Blood Flow Imaging Using an Autocorrelation Technique"; IEEE Transactions on Sonics Ultrasonics; May 1985; pp. 458-464; vol. SU-32, No. 3; IEEE.

"Prioritizing Interventions to Improve Rates of Thrombolysis for Ischemic Stroke"; Neurology: California Acute Stroke Pilot Registry Investigators; 2005; pp. 654-659; vol. 64; located at: www.neurology.org.

Roscitano, Antonino et al.; "Case Report: Acute Dysfunction from Thrombosis of a Mechanical Mitral Valve Prosthesis"; Braz J Cardiovasc Surg; 2005; pp. 88-90; vol. 20, No. 1; Dept. of Cardiac Surgery, St. Andrea Hospital, "La Sapienza" University, Rome, Italy.

Watrous, Raymond L. et al.; "Computer-Assisted Detection of Systolic Murmurs Associated with Hypertrophic Cardiomyopathy"; Tex Heart Inst J; 2004; pp. 368-375; vol. 31, No. 4.

Brill, S. et al.; "Bier's Block: 100 Years Old and Still Going Strong"; Acta Anaesthesiologica Scandinavica; 2004; pp. 117-122; vol. 48; Acta Anaesthesiol Scand.

Brown, Eli M. et al.; "A Case Report: Prolongad Intravenous Regional Anestesia"; Anestesia and Analgesia Current Researches; May-Jun. 1966; pp. 319-321; vol. 45; located at: http://www.anesth-analg.org/cgi/reprint/45/3/319.

"Exmocare: Answers to Frequently Asked Questions"; Exmocare; printed on Mar. 18, 2008; pp. 1-4; located at: http://www.exmocare.com/faq.

"Exmocare: BT2"; Exmocare; printed on Mar. 18, 2008; pp. 1-5; located at: http://www.exmocare.com/bt2/.

Mabee, John et al.; "Basic Investigations: Bier Block Exsanguination: A Volumetric Comparison and Venous Pressure Study"; Academic Emergency Medicine; Feb. 2000; pp. 105-113; vol. 7, No. 2; located at: http://www.ncbi.nlm.nih.gov/pubmed/10691067.

Moradkhan, Raman et al.; "Metabolic Forearm Vasodilation is Enhanced Following Bier Block with Phentolamine"; Am J Physiol Heart Circ Physiol; Aug. 3, 2007; pp. H2289-H2295; vol. 293; located at: http://ajpheart.physiology.org/cgi/content/abstract/293/4/H2289 (only abstract provided).

"Phase 1 of the BT2 is Now Complete"; Exmocare—Phase I of the BT2 vital signs wristwatch complete; printed on May 12, 2008; pp. 1-9; located at: http://www.exmocare.com/index.html.

Spanner, K.; "Survey of the Various Operating Principles of Ultrasonic Piezomotors"; Actuator 2006; pp. 1-8; located at; http://www.pi-usa.us/technotes/Actuator2006_SurveyoftheVariousOperatingPrinciplesofUltrasonicPiezomotors_c.pdf.

Taskaynatan, Mehmet Ali et al.; "Bier Block With Methylprednisolone and Lidocaine in CRPS Type I: A Randomized, Double-Blinded, Placebo-Controlled Study"; Regional Anesthesia and Pain Medicine; Sep.-Oct. 2004; pp. 408-412; vol. 29, No. 5; American Society of Regional Anesthesia and Pain Medicine.

Edwards, David et al.; "99mTc-NC100668, an Agent for Imaging Venous Thromboembolism: The Effect of Anticoagulant or Thrombolytic Therapy on the Upake and Retuntion of Radioactivity in Blood Clots in Vivio"; Nuclear Medicine Communications; dated 2007; pp. 55-62; vol. 28; Lippincott Williams & Wilkins.

Gatto, Rodolfo et al.; "Optical Microprobe for Blood Clot Detection"; Biomedical Optics, Technical Digest; dated Mar. 19, 2006; pp. 1-3; located at: http://www.opticsinfobase.org/abstract.cfm?URI=BIO-2006-ME47.

Gatto, Rodolfo et al.; "Optical Probe for Blood Clot Detection"; Journal of Applied Spectroscopy; dated 2007; pp. 1-19; located at; http://rodolfogatto.com/papers/Gatto_2007_Optical%20Probe_AS.pdf.

Greco, Frank A.; "Reflectance Spectroscopy of Clotting Blood: A Description of the Time-Dependent Behavior"; Arch Pathol Lab Med; Dated Feb. 2004; pp. 173-180; vol. 128.

He, Hongying et al.; "Computed Tomography Evaluation of Right Heart Dysfunction in Patients with Acute Pulmonary Embolism"; J. Comput Assist. Tomogr.; dated Mar./Apr. 2006; pp. 262-266; vol. 30, No. 2; Lippincott Williams & Wilkins.

Hart, James et al.; "P.O. Pro Wireless Reflectance Pulse Oximeter: Design 1"; dated Nov. 10, 2004; pp. 1-30; located at: www.bme.uconn.edu/sendes/Spring05/Team3/papers/design2.doc.

Hintz, Susan R. et al.; "Bedside Imaging of Intracranial Hemorrhage in the Neonate Using Light: Comparison with Ultrasound, Computed Tomography, and Magnetic Resonance Imagine"; Pediatric Research; dated May 1999; pp. 737-738; vol. 45; International Pediatrics Research Foundation, Inc.

Hunter, James B. et al.; "Methods of Anaesthesia Used for Reduction of Colles' Fractures"; BMJ; dated Nov. 25, 1989; pp. 1316-1317; vol. 299, No. 6711; located at; http://ukpmc.ac.uk/articlerender.cgi?artid=932375.

ISSYS: Integrated Sensing Systems—Press Release: ISSYS Receives Phase II SBIR Grant from NSF for Development of WaferScale, Mermetric, Hybrid Integration of MEMS and Electronics; dated Oct. 2, 2007; pp. 1-2.

ISSYS: Integrated Sensing Systems—Press Release: ISSY Receives Patent for Fuel & Fluid Quality Sensor; dated Sep. 18, 2007; pp. 1-2.

ISSYS: Integrated Sensing Systems—Press Release: ISSY Receives Patent for Fuel Cell Sensor; dated Aug. 21, 2007; pp. 1-2.

ISSYS: Integrated Sensing Systems—Press Release: NSF Awards a Phase I SBIR to ISSYS Inc. for Investigating Two-Phase Microfluidic Behavior and Nanoliter Bubble Dection; dated Jul. 17, 2007; pp. 1-2.

ISSYS: Integrated Sensing Systems—Press Release: ISSYS Inc. Awarded a Patent for Wireless, Batteryless, Implantable Sensors; dated Jul. 5, 2007; p. 1.

ISSYS: Integrated Sensing Systems—Press Release: ISSY to Present Fuel Cell Sensor Poster at the "SME Tomorrow's Energy . . . Today 2006" Conference; dated Oct. 3, 2006; pp. 1-2.

ISSYS: Integrated Sensing Systems—Press Release: ISSY Will Exhibit at the Medical Design & Manufacturing Exposition and Conference; dated Sep. 26, 2006; pp. 1-2.

ISSYS: Integrated Sensing Systems—Press Release: ISSYS Methanol Concentration Sensor to be Featured at the JAIMA Exposition; dated Aug. 29, 2006; pp. 1-2.

ISSYS: Integrated Sensing Systems—Press Release: ISSYS Awarded New Patent for a Resonant Tube Viscosity Sensing Device; dated Jun. 21, 2006; pp. 1-2.

Kim, Tae Min et al.; "Clinical Predictors of Recurrent Venous Thromboembolism: A Single Institute Experience in Korea"; Thrombosis Research; dated 2008; pp. 1-7; Elsevier Ltd.

Morris, Timothy A. et al.; "Improved Imaging of Deep Venous Thrombi During Anticoagulation Using Radiolabelled Anti-D-Dimer Antibodies"; Nuclear Medicine Communications; dated 2004; pp. 917-922; vol. 25; Lippincott Williams & Wilkins.

Parker, Martyn J.; "We Need Look Critically at Evidence for Universal Use"; BMJ; dated May 24, 2008; pp. 1145-1148; vol. 336; located at: http://www.bmj.com/cgi/content/short/336/7654/1148.

Rossow, Molly J. et al.; "Blood Flow Measurements and Clot Detection with Near-Infrared Spectroscopy"; Optics InfoBase—Conference Paper: Biomedical Topical Meeting, Ft. Lauderdale, FL; dated Mar. 19, 2006; pp. 1-3; OSA/BOSD, AOIMP, TLA.

Roumen-Klappe, E.M.; "Multilayer Compression Bandaging in the Acute Phase of Deep-Vein Thrombosis Has No Effect on the Development of the Post-Thrombotic Syndrome"; J. Thromb Thrombolysis; dated 2008; pp. 1-5; Springer.

So-Ling, Carmen et al.; "A Multi-Layered Reflection Model of Natural Human Skin"; CGI: Computer Graphics International; dated 2001; p. 0249; (only abstract provided).

Stone, Michael J. et al.; "Pulsed-High Intensity Focused Ultrasound Enhanced tPA Mediated Thrombolysis in a Novel in Vivo Clot Model, A Pilot Study"; Thromb Res.; dated 2007; pp. 193-202; vol. 121, No. 2; NIH Public Access Author Manuscript.

Vidal Melo, Marcos F. et al.; "Changes in Regional Ventilation Afer Autologus Blood Clot Pulmonary Embolism"; Anesthesiology; dated Sep. 2002; pp. 671-681; vol. 97, No. 3; American Society of Anesthesiologists, Inc.

Walsh, Fergus; "Scanner Spots Deadly Blood Clots"; BBC News; dated Apr. 13, 2007; pp. 1-3; located at: http://news.bbc.co.uk/2/hi/health/6541279.stm.

Wieringa F.P. et al.; "Remote Non-Invasive Stereoscopic Imaging of Blood Vessels: First In-Vivo Results of a New Multispectral Contrast Enhancement Technology"; Annals of Biomedical Engineering; dated Dec. 2006; pp. 1870-1878; vol. 34, No. 12; Biomedical Engineering Society.

Xie, Hua et al.; "Staging Deep Venous Thrombosis Using Ultrasound Elasticity Imaging: Animal Model"; Ultrasound in Med. & Biol.; dated 2004; pp. 1385-1396; vol. 30, No. 10; World Federation for Ultrasound in Medicine & Biology.

Zhang, Quan et al.; "Study of Near Infrared Technology for Intracranial Hematoma Detection"; Journal of Biomedical Optics; dated Apr. 2000; pp. 206-213; vol. 5, No. 2.

Dieter, Robert S. et al.; "Prosthetic Heart Valve Thrombosis: An Overview"; Wisconsin Medical Journal; Bearing a date of 2002; pp. 67-68; vol. 101, No. 7.

Landry, Anthony et al.; "Theoretical and experimental quantification of carotid plaque volume measurements made by three-dimensional ultrasound using test phantoms"; Medical Physics; bearing a date of Oct. 2002; pp. 2319-2327; vol. 29, No. 10; American Association Physical Medicine.

Mackinnon, Andrew D. et al.; "Long-Term Ambulatory Monitoring for Cerebral Emboli Using Transcranial Doppler Ultrasound"; STROKE; Journal of the American Heart Association; originally published Dec. 18, 2003; pp. 73-78; American Heart Association.

Weil, M. H.; "Defining Hemodynamic Instability"; Update in Intensive Care and Emergency Medicine; 2005; pp. 9-17, (2 page abstract printed on Aug. 16, 2011) ; vol. 42, part 2; (abstract located at: http://www.springerlink.com/content/lh3g72p32621125j/ ).

Baumgartner et al.; "Factors Controlling Thrombus Formation on Arterial Lesions"; Annals New York Academy of Sciences; Oct. 1985; pp. 162-177; vol. 454; Issue 1.

Smith et al.; "A Comparison of Four Methods for Distinguishing Doppler Signals From Gaseous and Particulate Emboli"; Journal of the American Heart Association; Jun. 1998; pp. 1133-1138; vol. 29; No. 6; American Heart Association; Dallas, TX.

Carter, J. Stein; "Circulatory System"; bearing a date of Nov. 13, 2006; pp. 1-5; http://biology.clc.uc.edu/courses/bio105/circulat.htm.

Thefreedictionary.com; "Tonometer"; bearing a date of 2012, printed on Jun. 13, 2012; pp. 1-4; Farlex, Inc.; http://medical-dictionary.thefreedictionary.com/tonometer.

\* cited by examiner

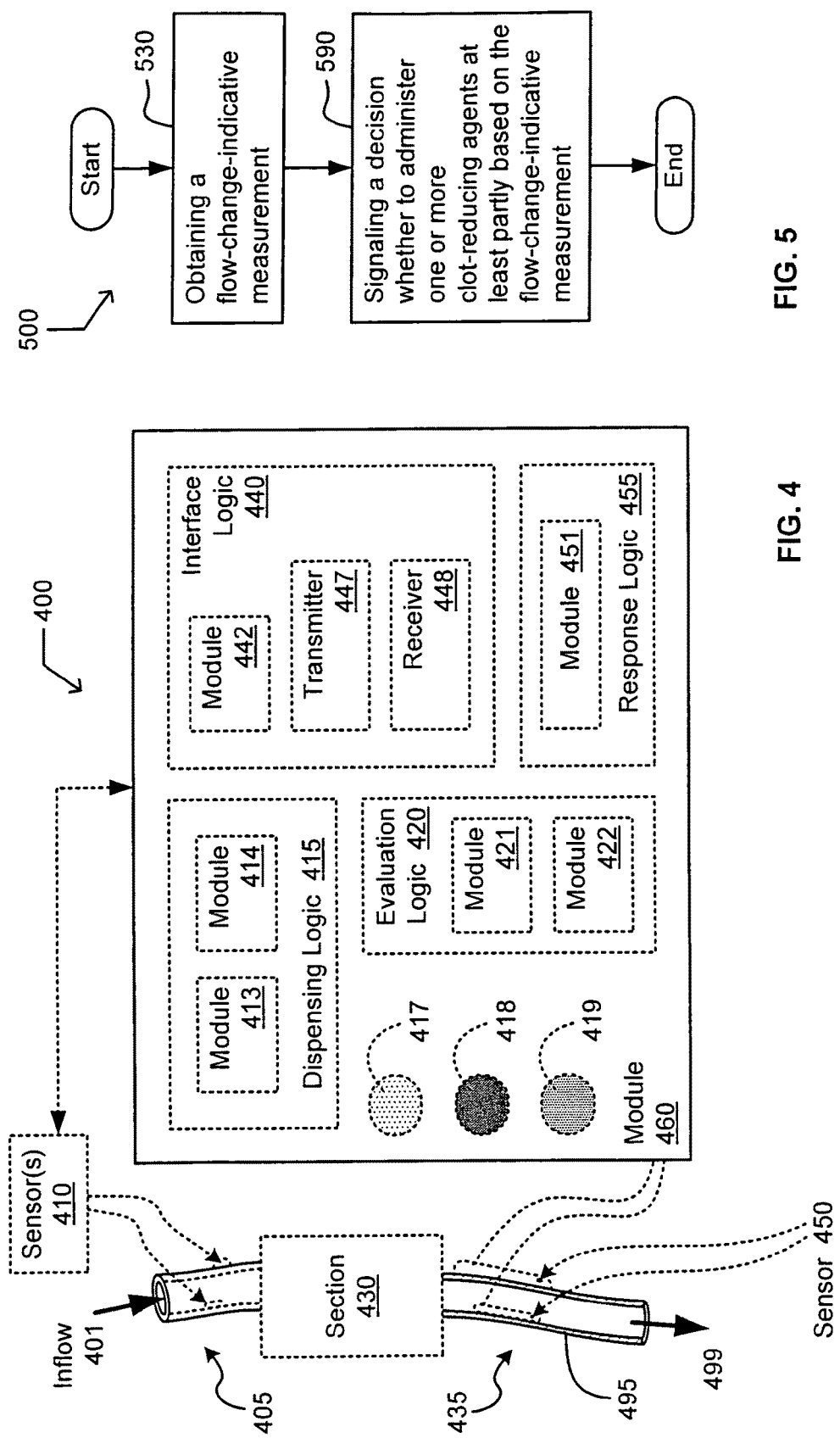

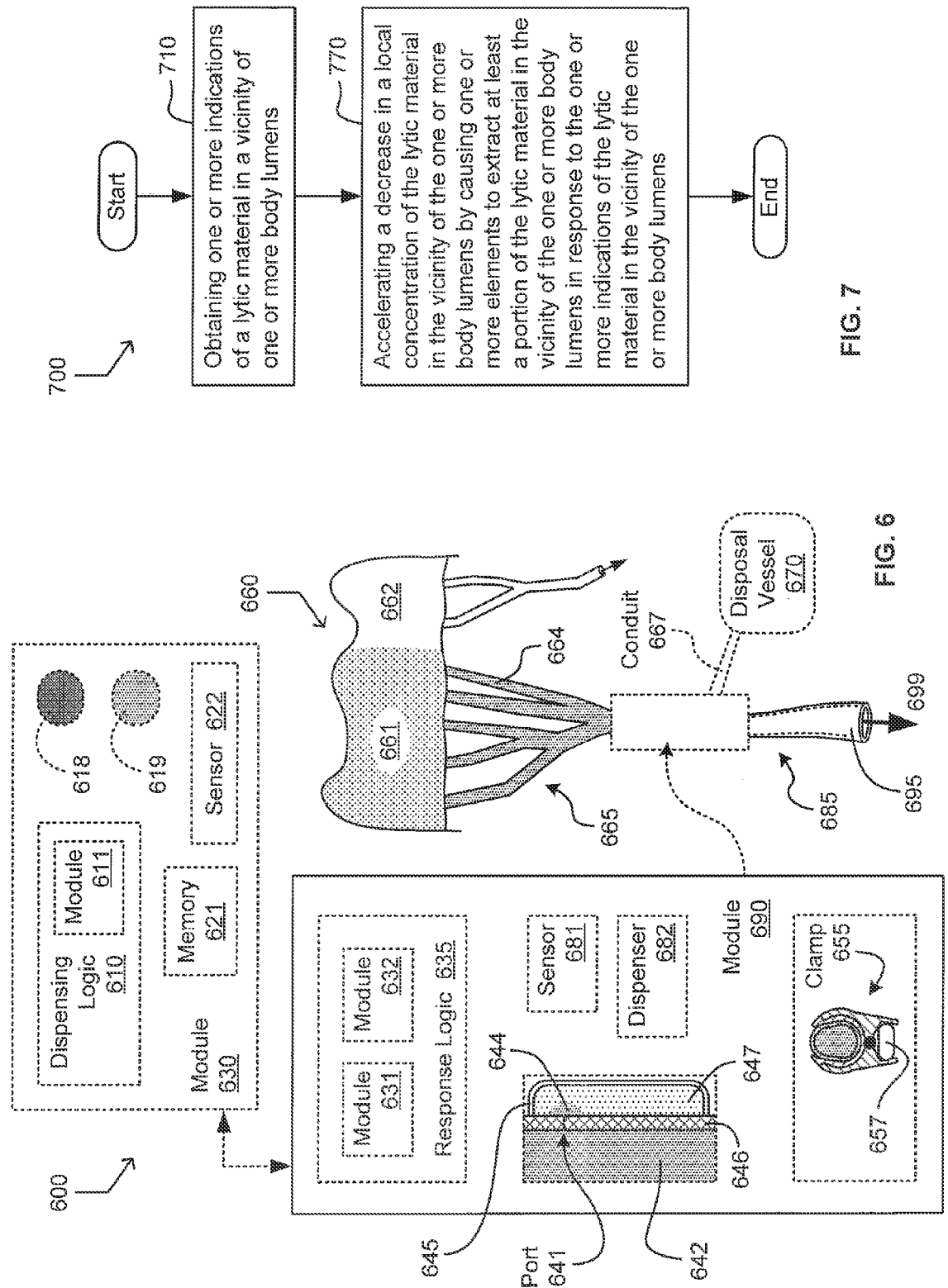

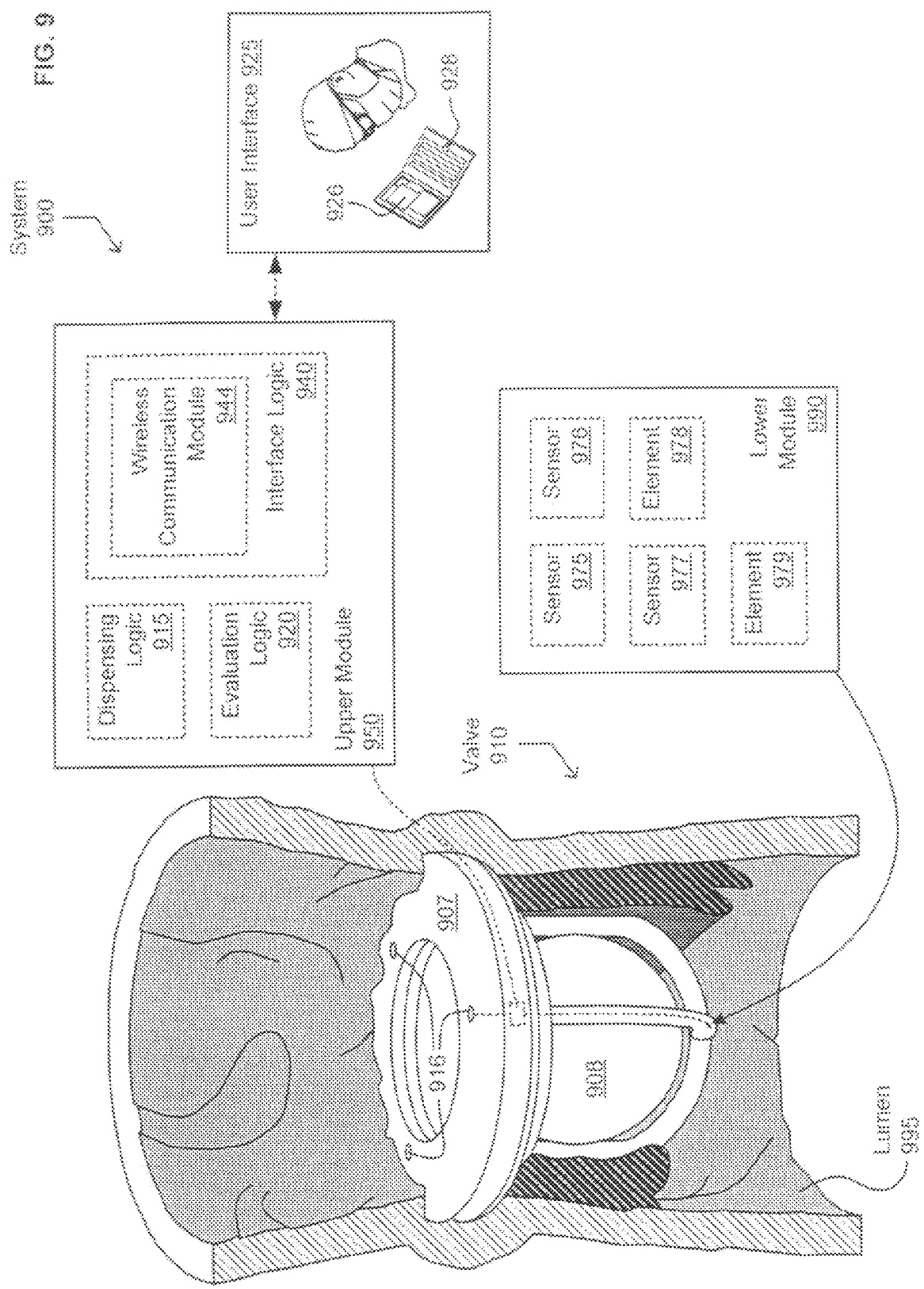

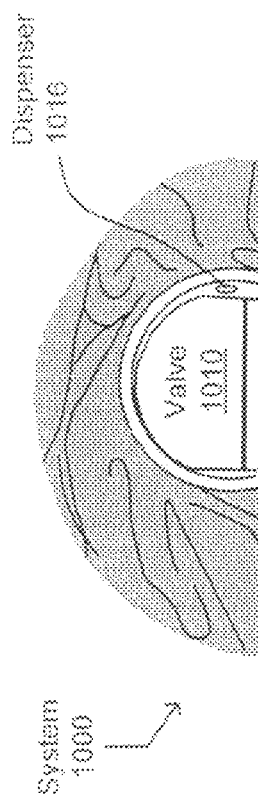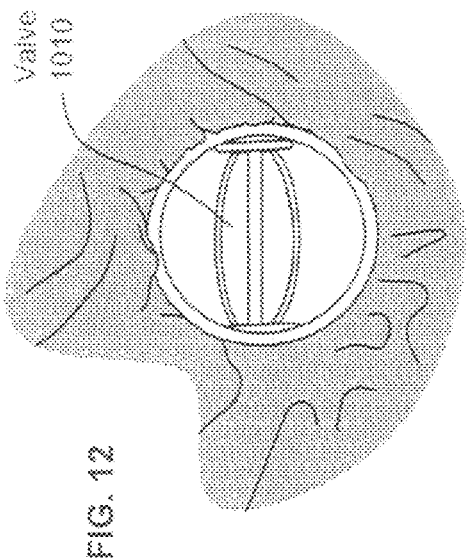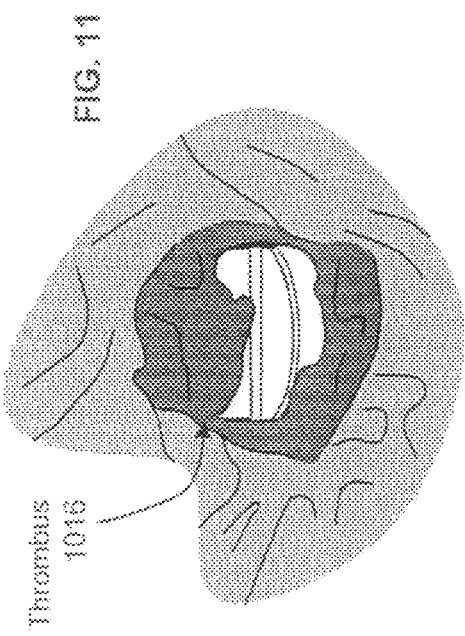

TREATMENT INDICATIONS INFORMED BY A *PRIORI* IMPLANT INFORMATION

CROSS-REFERENCE TO RELATED APPLICATIONS

The present application is related to and claims the benefit of the earliest available effective filing date(s) from the following listed application(s) (the "Related Applications") (e.g. claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/004,107, entitled TREATMENT INDICATIONS INFORMED BY A PRIORI IMPLANT INFORMATION, naming Bran Ferren, Roderick A. Hyde, Muriel Y. Ishikawa, Eric C. Leuthhardt, Dennis J. Rivet, Lowell L. Wood, Jr. and Victoria Y.H. Wood as inventors, filed Dec. 18, 2007, which a currently co-pending or is an application of which a currently co-pending application is entitled to the benefit of the filing date. The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

In one aspect, a method includes but is not limited to obtaining a priori implant information and signaling a decision whether to initiate implant-site-targeting treatment partly based on the a priori implant information and partly based on one or more other clot-indicative determinants. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to circuitry for obtaining a priori implant information and circuitry for signaling a decision whether to initiate implant-site-targeting treatment partly based on the a priori implant information and partly based on one or more other clot-indicative determinants. In addition to the foregoing, other system aspects are described in the claims, drawings, and text forming a part of the present disclosure.

In one aspect, a method includes but is not limited to obtaining a flow-change-indicative measurement and signaling a decision whether to administer one or more clot-reducing agents at least partly based on the flow-change-indicative measurement. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to circuitry for obtaining a flow-change-indicative measurement and circuitry for signaling a decision whether to administer one or more clot-reducing agents at least partly based on the flow-change-indicative measurement. In addition to the foregoing, other system aspects are described in the claims, drawings, and text forming a part of the present disclosure.

In one aspect, a method includes but is not limited to obtaining one or more indications of a lytic material in a vicinity of one or more body lumens and accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to circuitry for obtaining one or more indications of a lytic material in a vicinity of one or more body lumens and circuitry for accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens. In addition to the foregoing, other system aspects are described in the claims, drawings, and text forming a part of the present disclosure.

In one aspect, a system includes but is not limited to one or more capture components configured to accelerate a decrease in a local concentration of one or more therapeutic structures along a downstream portion of a vasculature and one or more dispensation components configured to release the one or more therapeutic structures into an upstream portion of the vasculature. In addition to the foregoing, other system aspects are described in the claims, drawings, and text forming a part of the present disclosure.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 4 depicts an exemplary environment in which one or more technologies may be implemented.

FIG. 5 depicts a high-level logic flow of an operational process.

FIG. 6 depicts an exemplary environment in which one or more technologies may be implemented.

FIG. 7 depicts a high-level logic flow of an operational process.

FIGS. 8-12 depict respective contexts in which one or more medical or veterinary technologies as described herein may be implemented.

DETAILED DESCRIPTION

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g. hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In the following detailed description, reference is made to the accompanying drawings, which form a part hereof. The use of the same symbols in different drawings typically indicates similar or identical items. The illustrative embodiments described in the detailed description, drawings, and claims are not meant to be limiting. Other embodiments may be utilized, and other chances may be made, without departing from the spirit or scope of the subject matter presented here.

Figure 1:
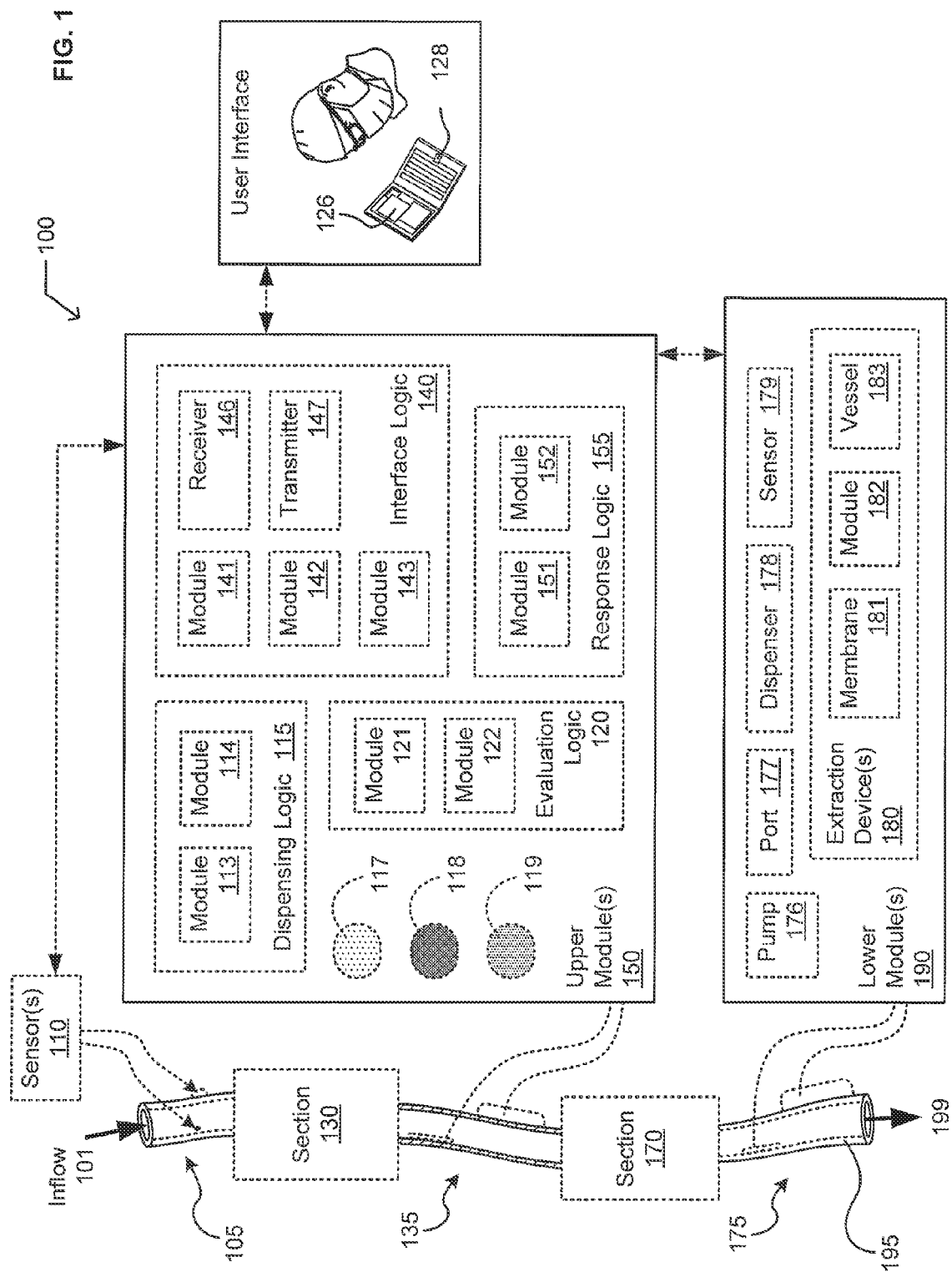
FIGS. 1-2 depict exemplary environments in which one or more technologies may be implemented.

With reference now to FIG. 1, shown is an example of a system that may serve as a context for introducing one or more processes and/or devices described herein. As shown system 100 may affect or otherwise relate to vicinity 105, section 130, vicinity 135, section 170, and vicinity 175 of a vascular lumen 195 through which one or more blood components may flow. One or more inflows 101 of blood enter respective portions of lumen 195 as shown, pass through sections 130, 170 and exit as one or more outflows 199. In respective variants, arteries, veins, or smaller vessels of lumen 195 may traverse proximities 105, 135, 175 as shown. Sections 130, 170 may likewise comprise one or more capillary beds as well as implants or other entities with which lumen 195 interacts.

In some variants, one or more upper modules 150 in vicinity 135 may (optionally) send data to and/or receive data from one or more instances of intravascular or other sensors 110 in vicinity 105. Upper module 150 may, likewise comprise one or more instances of modules 113, 114 of dispensing logic 115; dispensers 117, 118, 119; modules 121, 122 of evaluation logic 120; transmitters 147, receivers 148, or other modules 141, 142, 143 of interface logic 140; or modules 151, 152 of response logic 155. Interface logic may (optionally) handle data to output device 126 and/or from input device 128 as well interacting with one or more lower modules 190. Lower module 190 may include one or more instances of microfluidic or other pumps 176, ports 177, dispensers 178, sensors 179, or semi-permeable membranes 181 or other such modules 182 or vessels 183 of extraction devices 180.

Figure 2:
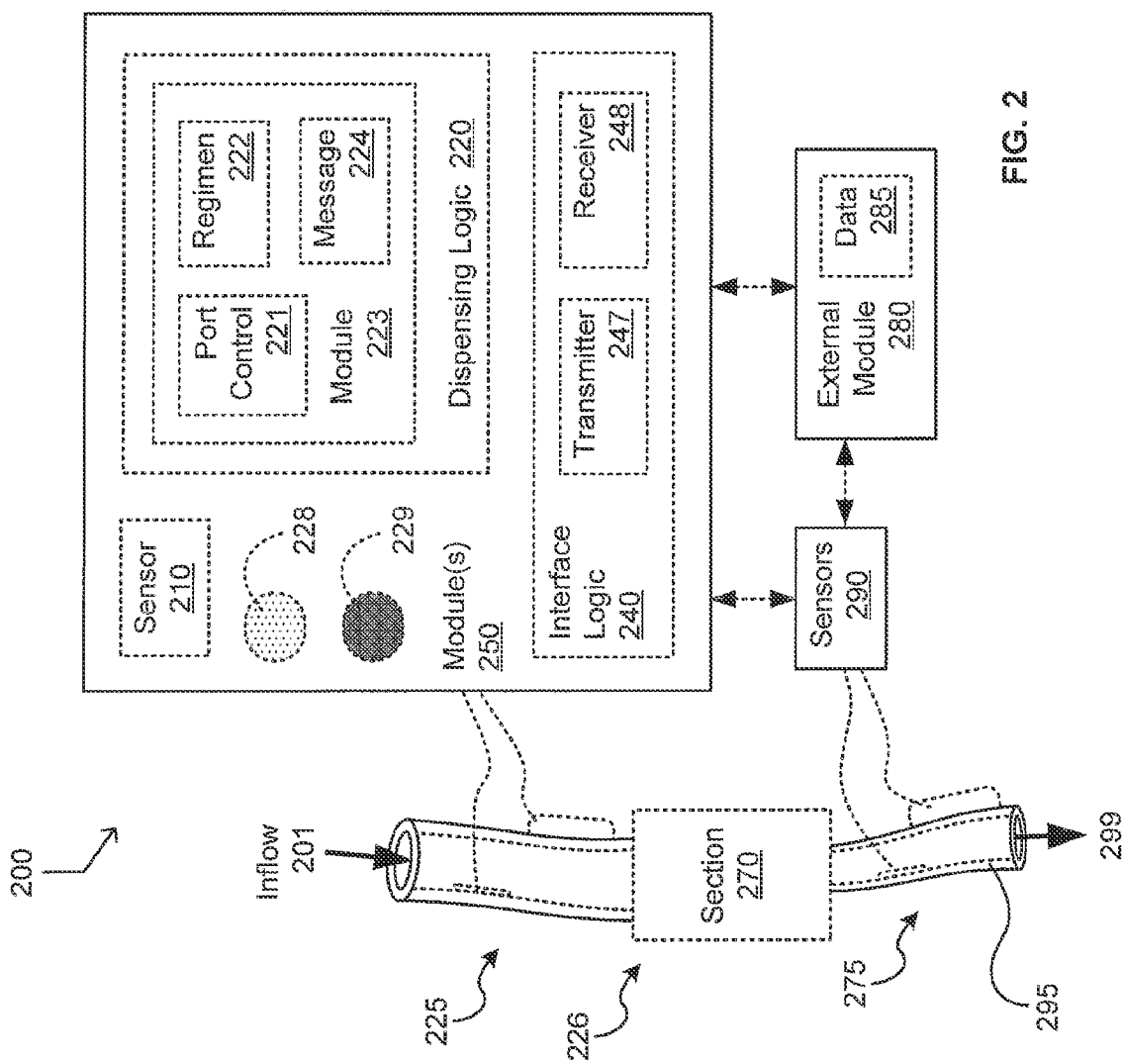

With reference now to FIG. 2, shown is an example of a system that may serve as a context for introducing one or more processes and/or devices described herein. As shown system 200 may affect or otherwise relate to vicinity 225, section 270, and vicinity 275 of a vascular lumen 295 through which one or more blood components may flow. One or more inflows 201 of blood enter respective portions of lumen 295 as shown, pass through section 270, and exit as one or more outflows 299. In respective variants, arteries, veins, or smaller vessels of lumen 295 may traverse proximities 225, 275 as shown. Section 270 may likewise comprise one or more capillary beds as well as vital organs and other tissues served by lumen 295.

In some variants, one or more intravascular or other modules 250 in vicinity 225 may (optionally) include one or more instances of sensors 210; modules 223 or other dispensing logic 220; dispensers 228, 229; or transmitters 247, receivers 248, or other interface logic 240. (Some such modules 250 may be operable for penetrating a vascular structure with ultrasonic or other energy, for example, or may comprise an implanted cannula or other transvascular structure.) Module 223 may, as shown, comprise one or more instances of port controls 221, regimens 222 or other programmatic dispensing information (optionally embodied in software or other instruction sequences, for example), or requests or other messages 224.

Alternatively or additionally, system 200 may comprise one or more intravascular or other sensors 290 that may (optionally) be configured to communicate (in one or both directions) with module 250, such as by a signal-bearing conduit or radio-frequency signal. (Some such sensors 290 may be operable for monitoring one or more physical phenomena within vascular structures, for example, from within or in a vicinity of the structures.) Systems 200 may likewise be configured to include or otherwise interact with one or more instances of external modules 280 operable, for example, for obtaining and providing data 285 as described herein. In some variants, for example, the one or more sensors 290 are only operable for communicating sensed analog or digital values to module 250. In others, one or more of the sensor(s) 290 are able to receive updates or other information from one or more external modules 280 or other transmitters 247 as described herein.

Figure 3:
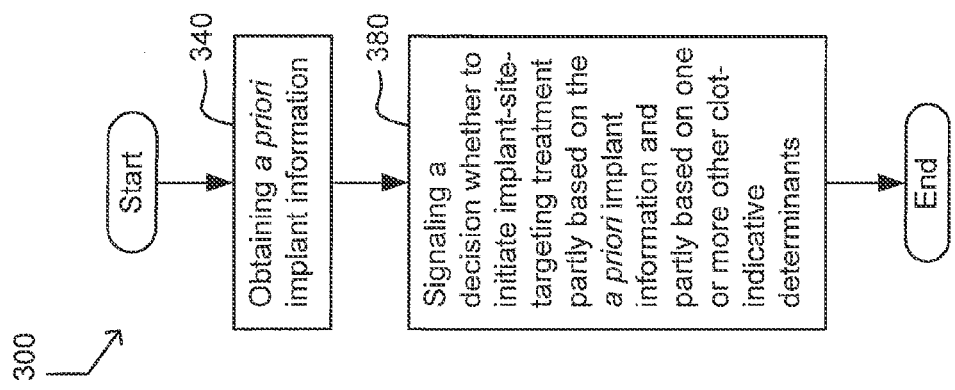
FIG. 3 depicts a high-level logic flow of an operational process.

With reference now to FIG. 3, shown is a flow 300 comprising operation 340—obtaining a priori implant information (e.g. receiver 248 receiving user-provided or other data 285 describing one or more sensors 290 or other implants downstream from one or more modules 250 in a vicinity 275 of lumen 295). This can occur, for example, in a context in which module 250 comprises a cannula or other implantable structure positioned upstream from an outflow 299 local to the implant(s) to which the a priori information pertains. Alternatively or additionally, receiver 248 may obtain sensor data or other determinants relating to such implants, as described herein.

Flow 300 further comprises operation 380—signaling a decision whether to initiate implant-site-targeting treatment partly based on the a priori implant information and partly based on one or more other clot-indicative determinants (e.g. interface logic 240 invoking one or more modules 223 of dispensing logic 220 operable for activating one or more dispensers 228 containing one or more thrombolytic agents or other locally-administered therapeutic materials selectively when apparently needed in a vicinity 275 of lumen 295). This can occur, for example, in a context in which the a priori implant information indicates a drug-eluting stent or other potentially thrombogenic implant at outflow 299.

With reference now to FIG. 4, shown is an example of a system that may serve as a context for introducing one or more processes and/or devices described herein. As shown system 400 may affect or otherwise relate to vicinity 405, section 430, and vicinity 435 of a subject's lumen 495 through which one or more blood components may flow. One or more inflows 401 of blood enter respective portions of lumen 495 as shown, pass through section 430, and exit as one or more outflows 499. In respective variants, arteries, veins, or smaller vessels of lumen 495 may traverse proximities 405, 435 as shown. Section 430 may likewise comprise one or more capillary beds as well as vital organs and other tissues served by lumen 495.

In some variants, module 460 may (optionally) include one or more instances of modules 413, 414 of dispensing logic 415; dispensers 417, 418, 419; modules 421, 422 of evaluation logic 420; interface logic 440; modules 451 or other response logic 455; or intravascular or other sensors 450. (Some such sensors 450 may be operable for monitoring radiant or other physical phenomena within a lumen 495, for example, from within or in a detection vicinity 405 of lumen 495.) Interface logic 440 may, as shown, comprise one or more instances of transmitters 447, receivers 448, or other modules 442 operable for communicating (in one or both directions) with one or more sensors 410 in (upstream) vicinity 405 of lumen 495.

With reference now to FIG. 5, shown is a flow 500 comprising operation 530—obtaining a flow-change-indicative measurement (e.g. one or more modules 421 of evaluation logic 420 detecting abnormally frequent blood pressure fluctuations for days consecutively). This can occur, for example, in a context in which a blood pressure fluctuation distribution for a specific pressure sensor is empirically determined and in which module 421 implements a threshold or other baseline derived by a reasonable statistical model. In some variants, for example, an appropriate normality threshold may be selected so that a frequency of occurrence or other measurable variable will be expected only to exceed the threshold once per decade (or similar duration within 1-2 orders of magnitude. Alternatively or additionally, a triggering condition may be selected in relation to one or more of optical, force, auditory, or other measurable criteria or to a combination of such criteria. Numerous reasonable triggering conditions will readily be apparent to those skilled in the art without undue experimentation, many of which are a mere matter of design choice in light of teachings herein.

Flow 500 further comprises operation 590—signaling a decision whether to administer one or more clot-reducing agents at least partly based on the flow-change-indicative measurement (e.g. one or more modules 413, 414 of dispensing logic 415 causing one or more dispensers 417, 418 to administer an antiplatelet-drug-containing or other therapeutic agent in response to the one or more modules 421, 422 of evaluation logic 420). This can occur, for example, in a context in which module 414 specifically selects such a therapeutic material by selecting the dispenser 418 containing the material in lieu of another dispenser. Alternatively or additionally, one or more modules 442 may be configured to signal the decision in some other way, such as by a speaker or other transmitter 447 conveying medication instructions to the (implanted) subject, or otherwise by sending such a message to a party who is able to implement the decision.

With reference now to FIG. 6, shown is an example of a system 600 that may serve as a context for introducing one or more processes and/or devices described herein, comprising one or more instances of module 630 operable for interacting with module 690. As shown, module 630 may include one or more modules 611 of dispensing logic 610 operable for controlling statin dispenser 618 or (other) therapeutic dispenser 619; memory 621 operable for handling software-implemented or other regimens; or one or more sensors 622 as described herein. Also shown is a kidney or other organ 660 having one or more (therapeutic-agent-) suffused portions 661 and one or more other portions 662, at least one of the suffused portions 661 comprising a vicinity 665 of (converging venules 664 of) lumen 695

Next downstream as shown, module 690 comprises one or more modules 631, 632 of response logic 635; (transvascular or other) extraction modules 645; sensors 681; dispensers 682; or clamps 655. As shown, extraction module 645 comprises one or more ports 641 to be formed through vessel wall 646, operable for extracting a portion 644 of lytic-material-infused blood 642, for example, into one or more absorbent elements 647 and/or to other disposal vessels at a lower-than-ambient pressure. As shown, one or more clamps 655 are configured to limit outflow 699 from module 690 by expanding one or more actuators 657, thereby levering lumen 695 to occlude it temporarily as shown. Alternatively or additionally, vicinity 685 of lumen 695 may include one or more conduits 667 operable for selectively removing a portion of outflow 699 by redirecting it to one or more artificial disposal vessels 670 as shown.

With reference now to FIG. 7, shown is a flow 700 comprising operation 710—obtaining one or more indications of a lytic material in a vicinity of one or more body lumens (e.g. module 631 of response logic 635 responding to a signal from one or more sensors 622, 681 or some other indication that an anticoagulant or other lactic material will apparently be present in a vicinity 665 of lumen 695). This can occur, for example, in a context in which response logic 635 receives a notification that one or more lytic-material-containing dispensers 619 have been activated. Alternatively or additionally, such indications can result from one or more sensors 681 detecting one or more natural chemical markers resulting from injury, for example. Alternatively or additionally, such indications can result from dispenser 682 administering a lytic compound by backflow into organ portion 661—injecting the compound at a somewhat higher pressure than that of blood in venules 664.

Flow 700 further comprises operation 770—accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens (e.g. port 641 or conduit 667 opening shortly after a dispensation of fibrinolytic material in upstream vicinity). This can occur, for example, in embodiments in which such ports or conduits are configured to allow higher-than-nominal concentrations of the lytic material to drain out of the vascular system, optionally by a timely exposure to an absorbent element 647 or other disposal vessel 670. Alternatively or additionally, such extraction may (optionally) be performed actively, such as by microfluidic or other pumps as described herein.

Figure 8:
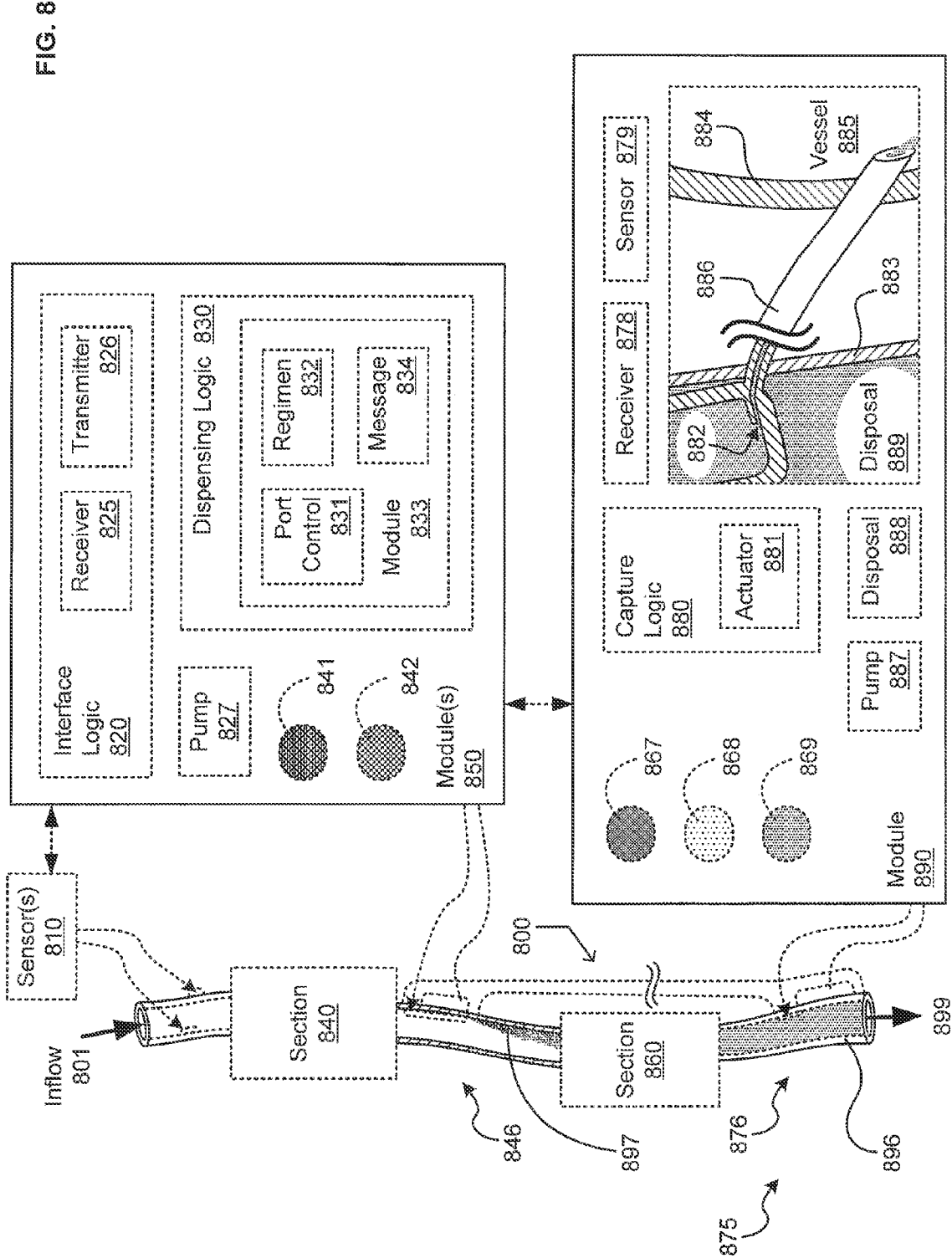

With reference now to FIG. 8, shown is an example of a system that may serve as a context for introducing one or more processes and/or devices described herein. As shown system 800 may affect or otherwise relate to one or more sections 840 or other "upstream" portions 846 of a human or other living subject's vasculature 896 (receiving inflow 801) and also to one or more "downstream" portions 876 of such vasculatures 896 (bearing outflow 899). One or more sections 840, 860 as shown may comprise one or more of capillary beds, tissues served by vasculature 896, or larger blood vessels as described above.

In some variants, one or more intravascular or other modules 850 may (optionally) include one or more instances of receivers 825, transmitters 826, or other interface logic 820 such as for communicating (in one or both directions) with one or more sensors 810 operable for monitoring upstream portion 846. Module 850 may likewise include one or more instances pumps 827 or other hardware controlled by dispensing logic 830 for selectively releasing one or more (biological, radiotherapy, or other) agents 841 or other therapeutic structures 842 into upstream portion 846. Such module(s) 850 may also be configured, in some contexts, by including one or more software or other modules 833 of dispensing logic 830 comprising one or more instances of port controls 831, (dispensing or other therapeutic) regimens 832, or messages 834 as described below.

As shown, system 800 may comprise one or more modules 850 upstream operable for communicating (in one or both directions) with one or more intravascular or other modules 890 downstream, optionally in an integral and/or implanted structure as shown. Alternatively or additionally, module 890 may include one or more instances of capture agents 867, 868 or other therapeutic agents 869; receivers 878; sensors 879; capture logic 880 operable for controlling one or more actuators 881, such as for optically or otherwise controlling the capture agent(s); pumps 887; or disposals 888, 889. As shown, for example, disposal 889 may include one or more ports 882 operable for accelerating a decrease in a local concentration of the agent(s) 841 or other therapeutic structure(s) 842 along portion 876 (downstream from dispensation 897, as shown) by allowing the structure(s) to pass into one or more conduits 886 traversing one or more vessel walls 883, 884. One or more vessels 885 configured to receive the structure(s) may include, in some embodiments, an esophagus or other natural vessels, implanted vessels, or ex situ vessels. Concerning the opening of port 641 or other timing of capture logic 880 or similar responsive circuitry described herein, a delay time between a capture site and an upstream site can be readily estimated with fair vasculature. A human blood cell typically travels about ⅓ of a millimeter per second in capillaries, for example. In some contexts, an accurate model may best be developed by measuring a specific interpositional delay empirically using, for example, a fluorescent material or other detectable measurement technique. Such a delay can readily be implemented in a digital or other timing feature of modules as described herein, for example, initiating a later operation at a programmed interval following a triggering event as described herein. In situations where a more reliable model is needed, a pulse-dependent, local-pressure-dependent, or other adaptive model may be appropriate, and well within the capabilities of skilled practitioners without undue experimentation in light of teachings herein.

With reference now to FIG. 9, shown is an example of a system that may serve as A context for introducing one or more processes and/or devices described herein. As shown system 900 may comprise a lumen 995 comprising an implantable valve 910 including an annular base 907 containing one or more dispensers 916, a ball 908, and one or more upper modules 950 and lower modules 990 operatively coupled as shown. Upper module 950 may comprise one or more instances of dispensation logic 915, evaluation logic 920, or wireless communication modules 944 or other interface logic 940 operable for communication with one or more user interfaces 925; for transmitting data to one or more output devices 926 or receiving data from one or more input devices 928 thereof as shown. Lower module 990 may comprise an optical sensor 975, an auditory sensor 976, or other sensors 977; or pressure or force sensors or other a flow-force-responsive elements 978 or other elements 979 as described herein.

An embodiment provides a system 900 comprising dispensing logic 915 or interface logic 940 operable for signaling a decision whether to initiate implant-site-targeting treatment and one or more dispensers 916 responsive to the decision. Each dispenser 916 may (optionally) include a thrombolytic agent and/or other therapeutic materials as described herein, suitable for targeting a vicinity of valve 910. The above-described "signaling" circuitry may comprise one or more of optical sensors 975, auditory sensors, flow-force-responsive elements 978, or other components suitable for providing thrombus-indicative measurements or other data suitable for informing the decision in light of teachings herein.

An embodiment provides a system 900 comprising interface logic 940 operable for signaling a decision (a) whether to initiate implant-site-targeting treatment or (b) whether to administer one or more clot-reducing agents. Alternatively or additionally system 900 comprising may similarly provide dispensing logic using such signaling, for example, for guiding one or more dispensers 916 accordingly. Each dispenser 916 may (optionally) contain a thrombolytic agent and/or other therapeutic materials as described herein, suitable for targeting a vicinity of valve 910. The above-described "signaling" circuitry may comprise one or more of optical sensors 975, auditory sensors, flow-force-responsive elements 978, or other components suitable for providing thrombus-indicative measurements or other data suitable for informing the decision in light of teachings herein.

With reference now to FIG. 10, shown is an example of a system that may serve as a context for introducing one or more processes and/or devices described herein. As shown system 1000 comprises (a top view of) a valve 1010 having a dispenser 1016 in an upper portion thereof. Any of the embodiments described herein with reference to FIG. 1 may effectively implement valve 1010 as a combination of upper module 150 and lower module 190 within lumen 195. Any of the embodiments described herein with reference to FIG. 2 may effectively implement valve 1010 as module 250 within lumen 295. Any of the embodiments described herein with reference to FIG. 4 mars effectively implement valve 1010 as module 460 within lumen 495. Any of the embodiments described herein with reference to FIG. 6 may effectively implement valve 1010 as module 690 within lumen 695. Any of the embodiments described herein with reference to FIG. 6 or 8 may likewise implement valve 1010 as module 690 or system 800 within lumen 695 or vasculature 896.

With reference now to FIG. 11, shown is (a bottom view of) a variant of valve 1010 in which a dangerous, partially occlusive thrombus 1016 has formed. An embodiment provides one or more sensors 179 in a lower module 190 suitable for detecting, thrombus 1016 and able to respond programmatically as described herein.

With reference now to FIG. 12, shown is (a bottom view of) a variant of valve 1010 in which thrombus 1016 has been prevented or removed as described herein. Valve 1010 is according operable for opening and closing effectively in this configuration, unlike that of FIG. 11.

Figure 13:
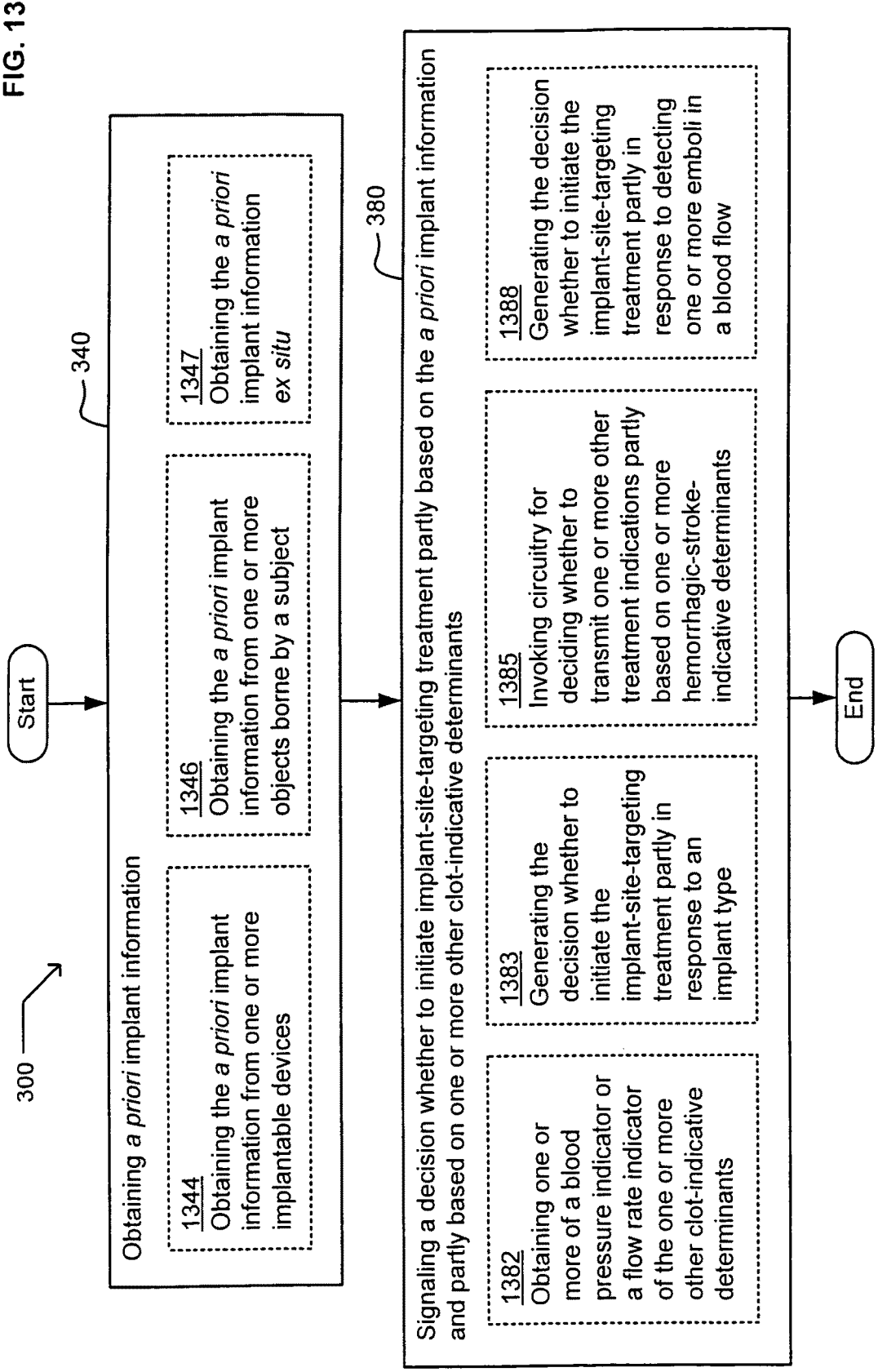
FIGS. 13-14 depict variants of the flow of FIG. 3.

With reference now to FIG. 13, there are shown several variants of the flow 300 of FIG. 3. Operation 340—obtaining a priori implant information—may (optionally) include one or more of the following operations: 1344, 1346, or 1347. In some embodiments, variants of operation 340 may (optionally) be performed by one or more instances of dispensing logic 115, 220, receivers 148, 248, or the like as exemplified herein. Operation 380—signaling a decision whether to initiate implant-site-targeting treatment partly based on the a priori implant information and partly based on one or more other clot-indicative determinants—may include one or more of the following operations: 1382, 1383, 1385 or 1388. In some embodiments, variants of operation 380 may be performed by one or more instances of dispensers 119, 229, transmitters 147, 247, or the like as described herein.

Operation 1344 describes obtaining the a priori implant information from one or more implantable devices (e.g. external module 280 receiving specifications or other data 285 about module 250 from a wireless or other transmitter 247 thereof). This can occur, for example, in a context in which external module 280 notifies locally-available caregivers of the existence of module 250 and/or of dispensations or dosages from it. Such information may be used to expedite care or avoid redundant dispensations, for example. Operation 1346 describes obtaining the a priori implant information from one or more objects borne by a subject. Operation 1347 describes obtaining the a priori implant information ex situ.

Operation 1382 describes obtaining one or more of a blood pressure indicator or a flows rate indicator of the one or more other clot-indicative determinants. Operation 1383 describes generating the decision whether to initiate the implant-site-targeting treatment partly in response to an implant type. Operation 1385 describes invoking circuitry for deciding whether to transmit one or more other treatment indications partly based on one or more hemorrhagic-stroke-indicative determinants. Operation 1388 describes generating the decision whether to initiate the implant-site-targeting treatment partly in response to detecting one or more emboli in a blood flow. Any of these operations may be omitted or performed before or during one or more instances or variants of operation 340 as described above, for example.

Figure 14:
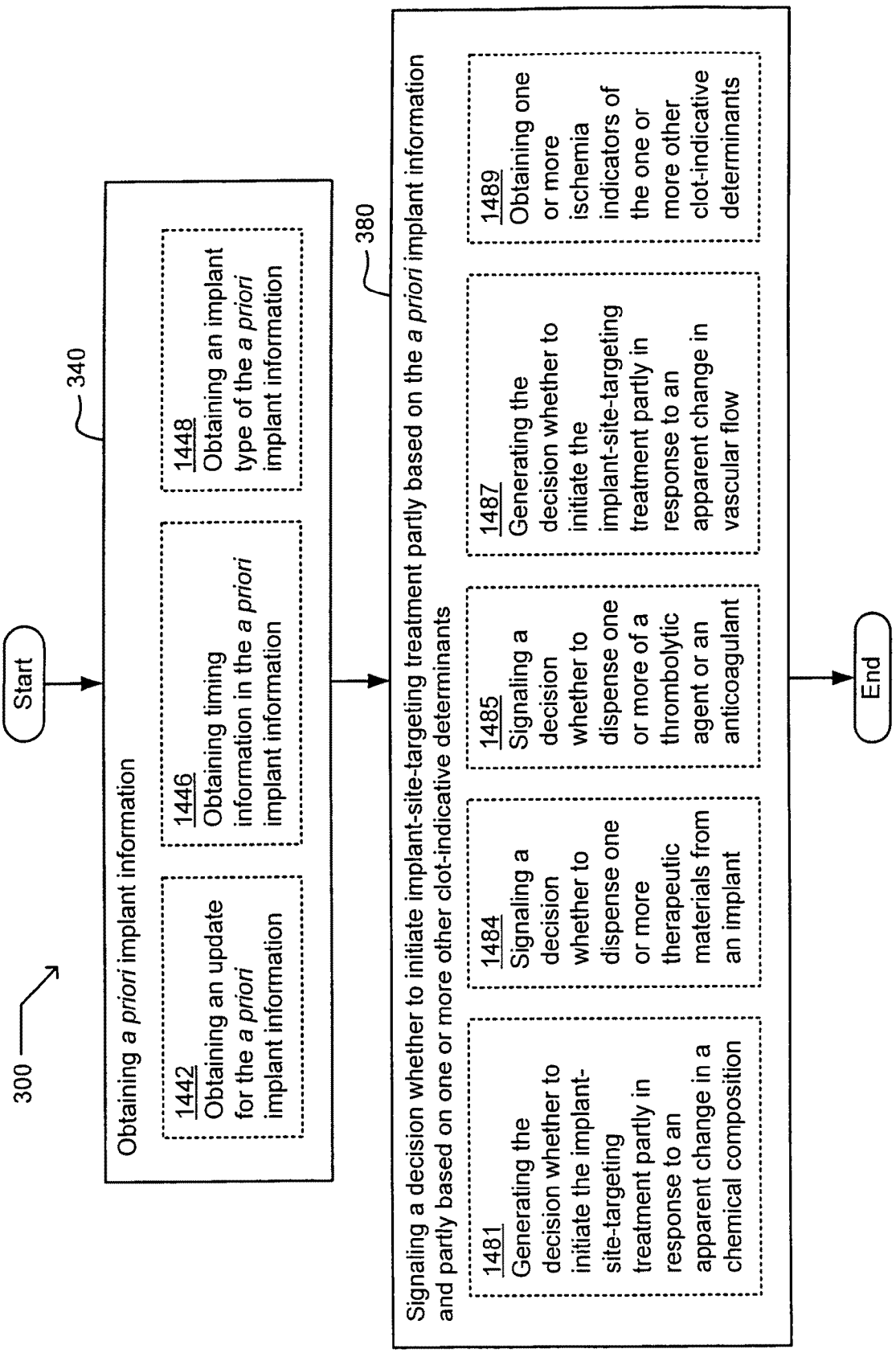

With reference now to FIG. 14, there are shown several variants of the flow 300 of FIG. 3 or 13. Operation 340—obtaining a priori implant information—may include one or more of the following operations: 1442, 1446, or 1448. In some embodiments, variants of operation 340 may be performed by one or more instances of dispensing logic 115, 220, receivers 148, 248, or the like as exemplified herein. Operation 380—signaling a decision whether to initiate implant-site-targeting treatment partly based on the a priori implant information and partly based on one or more other clot-indicative determinants—may include one or more of the following operations: 1481, 1484, 1485, 1487, or 1489. In some embodiments, variants of operation 380 may be performed by one or more instances of dispensers 119, 229, transmitters 147, 247, or the like as described herein.

Operation 1481 describes generating the decision whether to initiate the implant-site-targeting treatment partly in response to an apparent change in a chemical composition e.g. module 223 of dispensing logic 220 causing transmitter 247 to transmit a message 224 indicating one or more treatment materials (in dispensers 228, 229 as shown, e.g.) and/or a dispensation site 226 local to section 270 as a programmatic response to an apparently severe hypoxic condition or other circumstance detected via one or more sensors 210, 290 operable for detecting chemical concentrations). This can occur, for example, in a context in which a caregiver can validate and/or administer the dispensation of such a treatment material via an intravenous catheter. Alternatively or additionally, the decision to administer an already-implanted material may be performed according to a programmatic crisis-response regimen 222 specified in advance by a caregiver in response to an abnormally high platelet concentration detected locally, for example, by sensor 210.

Operation 1484 describes signaling a decision whether to dispense one or more therapeutic materials from an implant. Operation 1485 describes signaling a decision whether to dispense one or more of a thrombolytic agent or an anticoagulant. Operation 1487 describes generating the decision whether to initiate the implant-site-targeting treatment partly in response to an apparent change in vascular flow. Operation 1489 obtaining one or more ischemia indicators of the one or more other clot-indicative determinants.

Operation 1442 describes obtaining an update for the a priori implant information. Operation 1446 describes obtaining timing information in the a priori implant information. Operation 1448 describes obtaining an implant type of the a priori implant information. Any of these operations may be omitted or performed before, after, or interleaved with one or more instances or variants of operation 380 as described above, for example.

Figure 15:
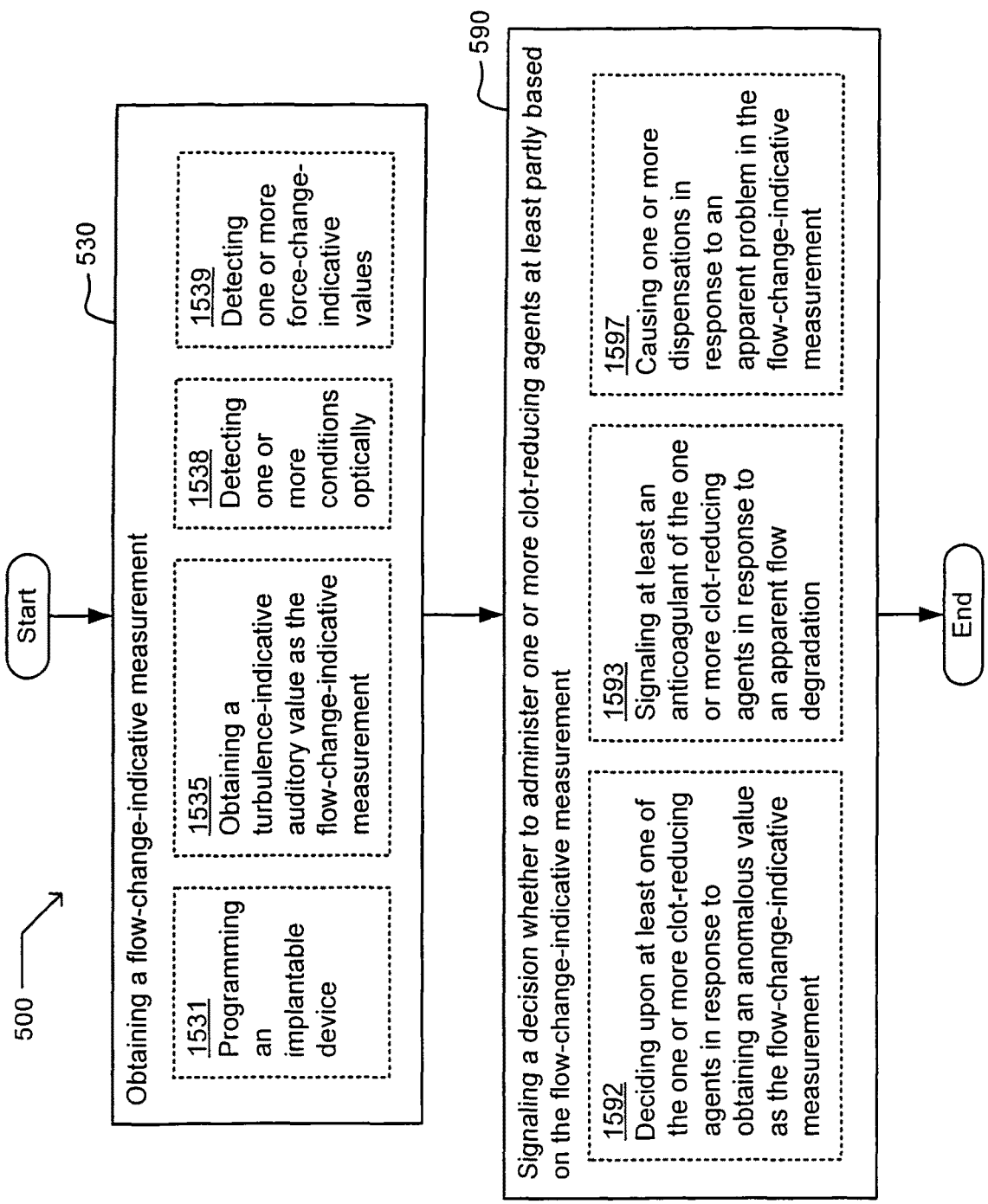
FIG. 15 depicts variants of the flow of FIG. 5.

With reference now to FIG. 15, there are shown several variants of the flow 500 of FIG. 5. Operation 530—obtaining a flow-change-indicative measurement—may (optionally)

include one or more of the following operations: 1531, 1535, 1538, or 1539. In some embodiments, variants of operation 530 may (optionally) be performed by one or more instances of sensors 179, 450, evaluation logic 120, 420, or the like as exemplified herein. Operation 590—signaling a decision whether to administer one or more clot-reducing agents at least partly based on the flow-change-indicative measurement—may include one or more of the following operations: 1592, 1593, or 1597. In some embodiments, variants of operation 590 may be performed by one or more instances of output devices 126, dispensing logic 115, 415, or the like as described herein.

As FIG. 15 indicates, (optional) operation 1531 describes programming an implantable device. Operation 1535 describes obtaining a turbulence-indicative auditory value as the flow-change-indicative measurement. Operation 1538 describes detecting one or more conditions optically. Operation 1539 describes detecting one or more force-change-indicative values. Operation 1592 describes deciding upon at least one of the one or more clot-reducing agents in response to obtaining an anomalous value as the flow-change-indicative measurement. Operation 1593 describes signaling at least an anticoagulant of the one or more clot-reducing agents in response to an apparent flow degradation. Operation 1597 describes causing one or more dispensations in response to an apparent problem in the flow-change-indicative measurement.

Figure 16:
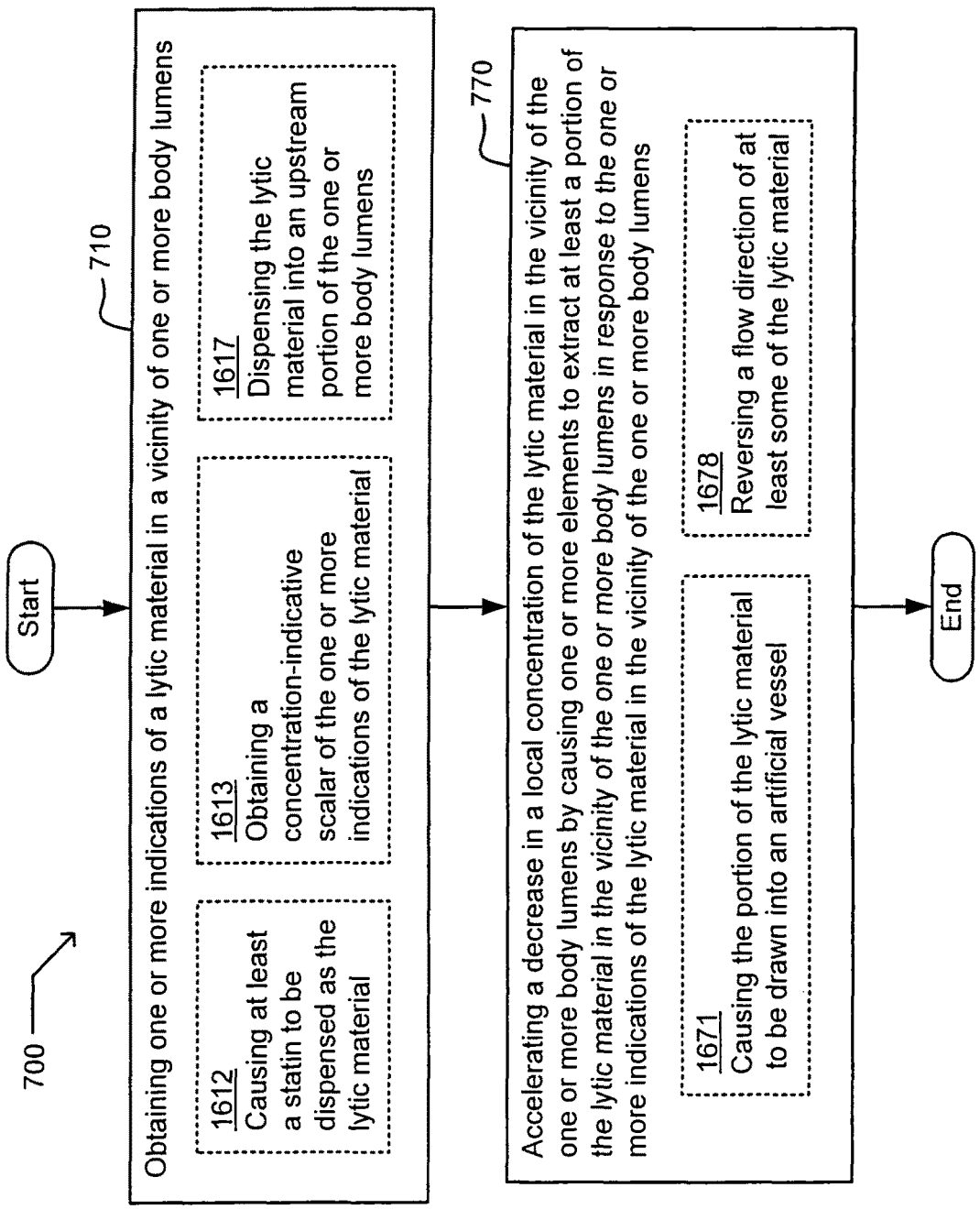
FIGS. 16-17 depict variants of the flow of FIG. 7.

With reference now to FIG. 16, there are shown several variants of the flow 700 of FIG. 7. Operation 710—obtaining one or more indications of a lytic material in a vicinity of one or more body lumens—may (optionally) include one or more of the following operations: 1612, 1613, or 1617. In some embodiments, variants of operation 710 may (optionally) be performed by one or more instances of sensors 110, 622, response logic 155, 635, or the like as exemplified herein. Operation 770—accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens—may include one or more of the following operations: 1671 or 1678. In some embodiments, variants of operation 770 may be performed by one or more instances of extraction device 180 or the like as described herein.

Operation 1612 describes causing at least a statin to be dispensed as the lytic material (e.g. dispensing logic 610 invoking module 611 or other circuitry for actuating statin dispenser 618 or other lytic-material-containing dispenser 619 according to one or more dosage profiles in memory 621). This can occur, for example, in embodiments in which one or more instances of modules 630 are positioned (locally) upstream from a lung or other organ 660 and in which at least a portion 661 of organ 660 has been perfused with an abnormally high concentration of lytic material (relative to a time-averaged systemic normal range, for example). Alternatively or additionally, in some variants, module 690 may be configured in a context in which one or more hemorrhage-risk determinants have been established in relation to one or more other organs in a downstream vicinity 685 of lumen 695 relative to outflow 699.

Operation 1613 describes obtaining a concentration-indicative scalar of the one or more indications of the lytic material (e.g. optical or other sensors detecting a gradational concentration measurement or other concentration-indicative value). This can occur, for example, in a context in which the lytic material includes a fluorescent or other readily detected marker material.

Operation 1617 describes dispensing the lytic material into an upstream portion of the one or more body lumens (e.g. an actuator urging tissue plasminogen activator or other lytic materials locally into a carotid or pulmonary artery responsive to an indication signifying sudden, substantial, apparent decrease of blood flow through that vessel). This can occur, for example, in a context in which one or more clots have blocked a majority of flow, in which one or more complementary or systemic determinants indicate an absence of substantial hemorrhaging, and in which a care provider has specified a preset, programmatic regimen by which such material(s) will be administered in these contingencies. Such complementary determinants may include a dangerously high local blood pressure or flow in complementary arteries, for example, of the pulmonary vasculature. Such systemic determinants may include substantial increases in (resting) heart rate or substantial decreases in blood pressure over a course of minutes or hours.

Operation 1671 describes causing the portion of the lytic material to be drawn into an artificial vessel (e.g. actuator 881 allowing one or more ports 882 to draw at least some of outflow 899 into one or more vessels 883 from lumen 895). This can occur, for example, in a context in which a dispenser has been dispensing a therapeutic material (agent 841, e.g.) containing one or more carcinogens or other ingredients having potentially undesirable side effects in outflow 899. Alternatively or additionally, a pump comprising conduit 886 may be used for accelerating a decrease of the local concentration of such materials within vicinity 875.

Operation 1678 describes reversing a flow direction of at least some of the lytic material (e.g. a pump reversing a material flow direction at least through a conduit). This can occur, for example, in a context in which a flow is apparently restored, such as may be manifested in a return to a normal local pressure in a formerly-blocked vessel or in a complementary vessel.

Figure 17:
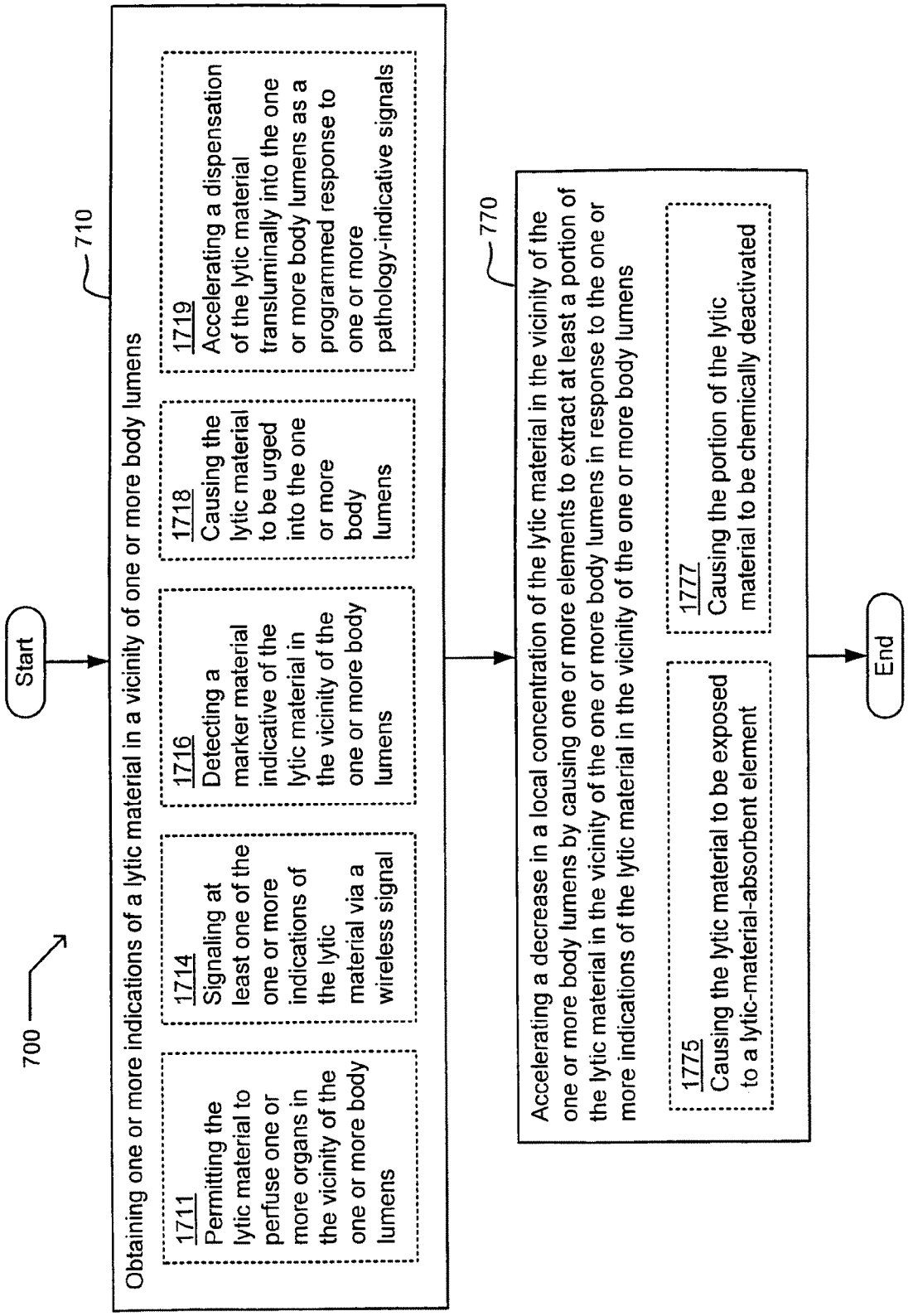

With reference now to FIG. 17, there are shown several variants of the flow 700 of FIG. 7 or 16. Operation 710—obtaining one or more indications of a lytic material in a vicinity of one or more body lumens—may (optionally) include one or more of the following operations: 1711, 1714, 1716, 1718, or 1719. In some embodiments, variants of operation 710 may (optionally) be performed by one or more instances of response logic 155, 635 or the like as exemplified herein. Operation 770—accelerating a decrease in a local concentration of the lytic material in the vicinity of the one or more body lumens by causing one or more elements to extract at least a portion of the lytic material in the vicinity of the one or more body lumens in response to the one or more indications of the lytic material in the vicinity of the one or more body lumens—may include one or more of the following operations: 1775 or 1777. In some embodiments, variants of operation 770 ma be performed by one or more instances of extraction device 180 or the like as described herein.

Operation 1711 describes permitting the lytic material to perfuse one or more organs in the vicinity of the one or more body lumens (e.g. dispensing logic 610 invoking one or more dispensers 619 to inject a lytic compound or other lytic material into a renal artery or otherwise to perfuse organ 660). This can occur, for example, in an embodiment in which dispensing logic 610 can invoke other logic modules and in which system 600 implements one or more devices like those disclosed in U.S. Pat. No. 6,592,567 ("Kidney perfusion catheter") or U.S. Pat. No. 6,514,226 ("Method and apparatus for treatment of congestive heart failure by improving perfusion of the kidney"). Alternatively or additionally, such a perfusion may reasonably be inferred at some time after a sufficiently large systemic administration of the lytic material. In some contexts this may be desirable, for example, even for a cancer patient for whom a lytic treatment in outflowed 699 presents a danger. In a case in which a majority of blood flowing through module 690 is removed from a patient's vasculature into one or more conduits 667, for example, a transfusion or other blood replacement at module 690 may be provided to supplement outflow 699 (optionally with a concomitant decrease in the local concentration of the lytic material).

Operation 1714 describes signaling at least one of the one or more indications of the lytic material via a wireless signal. Operation 1716 describes detecting a marker material indicative of the lytic material in the vicinity of the one or more body lumens. Operation 1718 describes causing the lytic material to be urged into the one or more body lumens. Operation 1719 describes accelerating a dispensation of the lytic material transluminally into the one or more body lumens as a programmed response to one or more pathology-indicative signals.

Operation 1775 describes causing the lytic material to be exposed to a lytic-material-absorbant element (e.g. an actuator opening a port so that lytic-material-containing fluid comes into contact with one or more foams, fabrics, fibers, or other such fluid-absorbant materials). Operation 1777 describes causing the portion of the lytic material to be chemically deactivated (e.g. dispenser releasing protease nexin or other such plasminogen activator inhibitors). This can occur, for example, in a context in which a force apparently induced by a clot has been detectably reduced after module has dispensed a local dose of a plasminogen activator or other such lytic material. In some contexts, a quantity of the inhibitor released may be sufficient to deactivate at least 0.1% to 1% (or at most about 5% to 50%) of a released quantity of the plasminogen activator.

In light of teachings herein, and referring again to FIG. 1, those skilled in the art will recognize that any of these systems may (optionally) include a variant in receiver 146 obtains a priori implant information by receiving configuration information to describe or otherwise accommodate a lower module 190 that has been or will be implanted. This can occur, for example, in a context in which one or more instances of upper module 150 is (or will be) well situated to administer one or more lytic materials or other therapies that may be needed at one or more instances of lower module 190. Alternatively or additionally, the a priori implant information may include implant status, material reservoir status or other such indications of modules as described herein.

Any of the above-described embodiments can likewise comprise a variant in which interface logic 140 invokes circuitry for performing operation 380 (of FIG. 3) such as one or more modules 113 of dispensing logic 115 operable for activating one or more dispensers 118, 119 when an apparent clot is detected. This can occur, for example, in a context in which the a priori implant information is embedded in circuitry or other structure of such dispensing logic 115.

Any of the above-described embodiments can likewise comprise a variant in which timing module 152 or another module 151 of response logic 155 performs operation 710 by responding to a signal from sensor 110 or some other indication that a lytic material will apparently be present in or near section 130 of lumen 195. This can occur, for example, in a context in which response logic 155 receives a notification that dispenser 119 has been activated. Alternatively or additionally, such indications may be received from one or more sensors 110 operable for detecting the lytic material directly or by detecting other such conditions as described herein. Alternatively or additionally, any of these modules or other components may likewise include a delay or other timing module 152 responsive to at least one of the one or more dispensation components. Alternatively or additionally, any of these modules or other components may likewise include one or more semi-permeable membranes 181.

Referring again to FIGS. 2-6, those skilled in the art will recognize that any of the herein-described modules or other components may likewise include one or more thrombolytic-agent-containing dispensers 228 and/or may include one or more (artificial) disposal vessels 670 and/or other features described with reference to FIG. 2 or 6. Referring again to FIG. 8, those skilled in the art will recognize that any such components may likewise include one or more disposals 888, optionally transluminal ones like disposal 889 in which one or more conduits 886 are configured to bear a blood-containing material into a body lumen. Any may likewise include one or more radiotherapy treatment modules or other such therapeutic structures 842.

Referring again to FIG. 9, alternatively or additionally, any of these modules or systems herein may likewise include an implantable, dispenser-containing valve 910. Any may likewise include one or more instances of wireless communication modules 944 for sending data to or receiving data from an outside network or other entity. Any may likewise include one or more optical sensors 975, auditory sensors 976, pressure sensors, pressure-limiting valves, strain gauges, or other such flow-force-responsive elements 978. Alternatively or additionally, any of these extraction modules or other material movement components may likewise comprise a lower-than-ambient pressure, at least initially. Alternatively or additionally, any of the above-described modules or other components may (optionally) include one or more implant-site-targeting dispensers, positioned for dispensing (a) above an implant of interest or (b) from an upstream or intermediate portion of the implant of interest.

Figure 18:
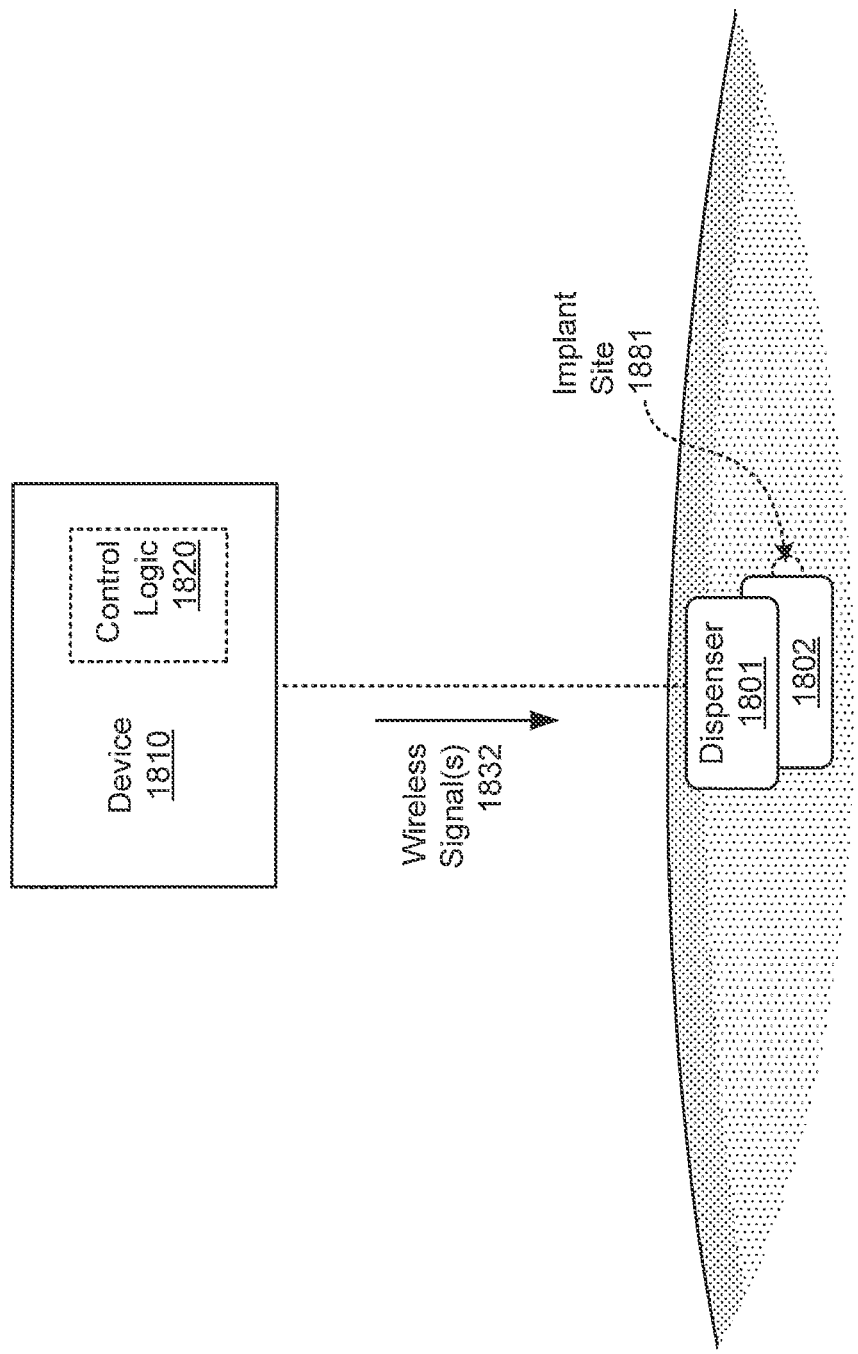
FIG. 18 depicts variants of the flow of FIG. 5.

With reference now to FIG. 18, shown is system in which one or more technologies may be implemented comprising at least one device 1810 operable for communication to one or more dispensers 1801, 1802 (comprising an implantable valve, e.g.) via one or more wireless signals 1832, in which control logic 1820 performs operation 530. In some variants, such systems may include a first dispenser 1801 operable for dispensing lytic material, a second dispenser 1802 operable for targeting an implant site 1881, and a device 1810 operable for communicating a selection (as wireless signal 1832, e.g.) of one or more of the first dispenser or the second dispenser. This exemplifies a first dispenser operable for dispensing at least the lytic material, a second dispenser operable for targeting an implant site, and a wireless-communication device operable for communicating a selection of one or more of the first dispenser or the second dispenser.

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.) (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"), the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A therapeutic administration system comprising:
   one or more modules for obtaining a flow-change indicative measurement;
   one or more modules for signaling a decision whether to administer one or more clot-reducing agents at least partly based on the flow-change-indicative measurement;
   a first dispenser operable for dispensing at least a lytic material;
   a second dispenser operable for targeting an implant site; and
   a wireless-communication device operable for communicating a selection of the first dispenser or the second dispenser.

2. The therapeutic administration system of claim 1 in which the one or more modules for obtaining a flow-change-indicative measurement comprise:
   a module for programming an implantable device.

3. The therapeutic administration system of claim 1 in which the one or more modules for obtaining a flow-change-indicative measurement comprise:
   a turbulence-indicative auditory valve as the flow-change-indicative measurement.

4. The therapeutic administration system of claim 1 in which the one or more modules for obtaining a flow-change-indicative measurement comprise:
   a module for detecting one or more conditions optically.

5. The therapeutic administration system of claim 4 in which the one or more modules for obtaining a flow-change-indicative measurement comprise:
   a turbulence-indicative auditory value as the flow-change-indicative measurement.

6. The therapeutic administration system of claim 1 in which the one or more modules for obtaining a flow-change-indicative measurement comprise:
   a module for detecting one or more force-change-indicative values.

7. The therapeutic administration system of claim 6 in which the one or more modules for signaling a decision whether to administer one or more clot-reducing agents at least partly based on the flow-change-indicative measurement comprise:
   a module for causing one or more dispensations in response to an apparent problem in the flow-change-indicative measurement.

8. The therapeutic administration system of claim 6, further comprising:
   a thrombolytic-agent-containing dispenser responsive to the decision whether to administer the one or more clot-reducing agents.

9. The therapeutic administration system of claim 1 in which the one or more modules for signaling a decision whether to administer one or more clot-reducing agents at least partly based on the flow-change-indicative measurement comprise:
   a module for deciding upon at least one of the one or more clot-reducing agents in response to obtaining an anomalous value as the flow-change-indicative measurement.

10. The therapeutic administration system of claim 1 in which the one or more modules for signaling a decision whether to administer one or more clot-reducing agents at least partly based on the flow-change-indicative measurement comprise:

a module for signaling at least an anticoagulant of the one or more clot-reducing agents in response to an apparent flow degradation.

11. The therapeutic administration system of claim 10 in which the one or more modules for signaling a decision whether to administer one or more clot-reducing agents at least partly based on the flow-change-indicative measurement comprise:

a module for one or more dispensations in response to an apparent problem in the flow-change-indicative measurement.

12. The therapeutic administration system of claim 1 in which one or more modules for signaling a decision whether to administer one or more clot-reducing agents at least partly based on the flow-change-indicative measurement comprise:

one or more instructions responsive to a flow-force-responsive element.

13. The therapeutic administration system of claim 1 in which the one or more modules for signaling a decision whether to administer one or more clot-reducing agents at least partly based on the flow-change-indicative measurement comprise:

one or more instructions responsive to an optical sensor.

14. The therapeutic administration system of claim 13, further comprising:

a thrombolytic-agent-containing dispenser responsive to the decision whether to administer the one or more clot-reducing agents.

15. The therapeutic administration system of claim 1 in which the one or more modules for signaling a decision whether to administer one or more clot-reducing agents at least partly based on the flow-change-indicative measurement comprise:

one or more instructions responsive to an auditory sensor.

16. The therapeutic administration system of claim 1 in which the one or more modules for signaling a decision whether to administer one or more clot-reducing agents at least partly based on the flow-change-indicative measurement comprise:

a module for causing one or more dispensations in response to an apparent problem in the flow-change-indicative measurement.

17. The therapeutic administration system of claim 1, further comprising:

a thrombolytic-agent-containing dispenser responsive to the decision whether to administer the one or more clot-reducing agents.

18. The therapeutic administration system of claim 1, further comprising:

an implant-site-targeting dispenser responsive to the decision whether to administer the one or more clot-reducing agents.

19. The therapeutic administration system of claim 1 in which the one or more modules for signaling a decision whether to administer one or more clot-reducing agents at least partly based on the flow-change-indicative measurement comprise:

a module for signaling at least an anticoagulant of the one or more clot-reducing agents in response to an apparent flow degradation.

20. A therapeutic administration system comprising:

one or more modules for obtaining a flow-change-indicative measurement;

one or more modules for signaling a decision whether to administer one or more clot-reducing agents at least partly based on the flow-change-indicative measurement;

a first dispenser operable for dispensing at least a clot-reducing agent;

a second dispenser operable for targeting an implant site; and a wireless-communication device operable for communicating a selection of the first dispenser or the second dispenser.

21. A therapeutic administration method comprising:

obtaining a flow-change-indicative measurement;

signaling a decision whether to administer one or more clot-reducing agents at least partly based on the flow-change-indicative measurement;

dispensing, from a first dispenser, at least a lytic material;

targeting, utilizing a second dispenser, an implant site and communicating, using a wireless-communication device, a selection of the first dispenser or the second dispenser.

* * * * *